United States Patent
Garin-Shkolnik

(10) Patent No.: US 12,226,398 B2
(45) Date of Patent: Feb. 18, 2025

(54) FABP4 AS A THERAPEUTIC TARGET IN SKIN DISEASES

(71) Applicant: TICURE LTD., Netanya (IL)

(72) Inventor: Tali Garin-Shkolnik, Timrat (IL)

(73) Assignee: TICURE LTD., Netanya (IL)

( * ) Notice: Subject to any disclaimer, the term of this patent is extended or adjusted under 35 U.S.C. 154(b) by 125 days.

(21) Appl. No.: 17/553,253

(22) Filed: Dec. 16, 2021

(65) Prior Publication Data

US 2022/0096435 A1 Mar. 31, 2022

Related U.S. Application Data

(62) Division of application No. 16/344,705, filed as application No. PCT/IL2017/051168 on Oct. 25, 2017, now Pat. No. 11,229,624.

(60) Provisional application No. 62/412,487, filed on Oct. 25, 2016.

(51) Int. Cl.
| | |
|---|---|
| *A61K 31/403* | (2006.01) |
| *A61K 31/415* | (2006.01) |
| *A61K 31/7105* | (2006.01) |
| *A61K 31/713* | (2006.01) |
| *A61P 17/00* | (2006.01) |
| *C12Q 1/6883* | (2018.01) |
| *A61K 9/00* | (2006.01) |
| *A61K 45/06* | (2006.01) |

(52) U.S. Cl.
CPC ......... *A61K 31/403* (2013.01); *A61K 31/415* (2013.01); *A61K 31/7105* (2013.01); *A61K 31/713* (2013.01); *A61P 17/00* (2018.01); *C12Q 1/6883* (2013.01); *A61K 9/0014* (2013.01); *A61K 9/0019* (2013.01); *A61K 45/06* (2013.01); *G01N 2800/20* (2013.01)

(58) Field of Classification Search
CPC .................................................. A61K 31/403
See application file for complete search history.

(56) References Cited

U.S. PATENT DOCUMENTS

| | | | |
|---|---|---|---|
| 6,548,529 B1 | 4/2003 | Robl et al. | |
| 6,927,227 B2 | 8/2005 | Robl et al. | |
| 8,748,470 B2 * | 6/2014 | Lengyel ............. | A61K 31/4155 514/19.2 |
| 2003/0199563 A1 | 10/2003 | Robl et al. | |
| 2009/0263792 A1 | 10/2009 | Miyata et al. | |
| 2012/0289570 A1 | 11/2012 | Lengyel et al. | |
| 2014/0363522 A1 | 12/2014 | Lengyel et al. | |
| 2016/0113937 A1 | 4/2016 | Wan et al. | |

FOREIGN PATENT DOCUMENTS

| | | | |
|---|---|---|---|
| EP | 1 707 199 A1 | | 10/2006 |
| WO | WO0059506 | * | 3/2000 |
| WO | 00/59506 A1 | | 10/2000 |

OTHER PUBLICATIONS

Garin-Shkolnik et al. Diabetes, 2014, 63:900-911.*
Lindegard's Dermatologica, 1986, 172(6): 298-304(abstract).*
Japanese Office Action, for Application No. 2019532962, issued Sep. 28, 2021, 5 pages, with English translation.
Furuhashi et al., "Lipid Chaperones and Metabolic International", International Journal of Inflammation, 642612, pp. 1-12 (2011).
Mastrofrancesco et al., "Preclinical Studies of a Specific PPARγ Modulator in the Control of Skin Inflammation", Journal of Investigative Dermatology, 134, pp. 001-1011, (2014).
Baran et al., "Serum Fatty Acid-Binding Protein 4 is Increased in Patients with Psoriasis", Lipids, vol. 52, pp. 51-60, 2017.
Burak et al., "Development of a therapeutic monoclonal antibody that targets secreted fatty acid-binding protein aP2 to treat type 2 diabetes", Sci Transl Med, vol. 7, Issue 319, 319ra205, 19 Pages, 2015.
Cao et al., "Adipocyte Lipid Chaperone aP2 is a Secreated Adipokine Regulating Hepatic Glucose Production", Cell Metab, vol. 17, pp. 768-778, 2013.
Chamcheu et al., "Upregulation of P13K/AKT/mTOR, FABP5 and PPARbeta/delta in Human Psoriasis and Imiquimod-induced Murine Psoriasiform Dermatitis Model", Acta Derm Venereol, vol. 96, No. 6, pp. 854-856, 2016.
Coe et al., "Physiological properties and functions of intracellular fatty acid-binding proteins", Biochim Biophys Acta, vol. 1391, No. 3, pp. 287-306, 1998.
Floresta et al., "Adipocyte fatty acid binding protein 4 {FABP4) inhibitors. A comprehensive systemic review", Eur J Med Chem, vol. 138, pp. 854-873, 2017.
Furuhashi et al., "Treatment of diabetes and atherosclerosis by inhibiting fatty-acid-binding protein aP2", Nature, vol. 447, No. 7147, pp. 959-965, 2007.
Furuhash I et al., "Fatty acid-binding proteins: role in metabolic diseases and potential as drug targets", Nat Rev Drug Discov, vol. 7, No. 6, pp. 489-503, 2008.
Garin-Shkolnik et al., "FABP4 Attenuates PPARgamma and Adipogenesis and Is Inversely Correlated with PPARgamma in Adipose Tissues", Diabetes, vol. 63, No. 3, pp. 900-911, 2014.
Guttman-Yassky et al., "Contrasting pathogenesis of atopic dermatitis and psoriasis—Part I: Clinical and pathologic concepts", J Allergy Immunol, vol. 127, No. 5, pp. 1110-1118, 2011.
Hotamisligil et al., "Uncoupling of Obesity from Insulin Resistance Through a Targeted Mutation in aP2, the Adipocyte Fatty Acid Binding Protein", Science, vol. 274, No. 5291, pp. 1377-1379, 1996.
Krueger et al., "Psoriasis pathophysiology: current concepts of pathogenesis", Annals of the Rheumatic Diseases, 64), 30-36, 2005.
Lan et al., "Small-molecule inhibitors of FABP4/5 ameliorate dyslipidemia but not insulin resistance in mice with dietnduced obesity", Journal of Lipid Research, vol. 52, No. 4, pp. 646-656, 2011.

(Continued)

*Primary Examiner* — Rei Tsang Shiao
(74) *Attorney, Agent, or Firm* — FISHERBROYLES, LLP; Roger L. Browdy

(57) ABSTRACT

Provided are methods of regulating proliferation and/or differentiation of keratinocytes and immune cells, more specifically to methods of treating pathologies characterized by hyperproliferative keratinocytes or inflammatory skin diseases by administration of FABP4-inhibitor.

18 Claims, 11 Drawing Sheets

Specification includes a Sequence Listing.

(56) References Cited

OTHER PUBLICATIONS

Look et al., "BMS309403 directly suppresses cardiac contractile function", Nauyn-Shmiedeberg's Arch Pharmacol, vol. 384, pp. 255-263, 2011.
Madsen et al., "Molecular Cloning and Expression of a Novel Keratinocyte Protein (Psoriasis-associated fatty acid-binding protein [PA-FABP]) that Is Highly Up-Regulated in Psoriatic Skin and that Shares Similarity to Fatty Acid-Binding Proteins", J Invest Dermatol, vol. 99, No. 3, pp. 299-305, 1992.
Maeda et al., "Adipocyte/macrophage fatty acid binding proteins control integrated metabolic responses in obesity and diabetes", Cell Metab, vol. 1, No. 2, pp. 107-119, 2005.
Miao et al., "The mAb against adipocyte fatty acid-binding protein 2E4 attenuates the inflammation in the mouse model of high-fat diet-induced obesity via toll-like receptor 4 pathway", Mol Cell Endocrinol, vol. 403, pp. 1-9, 2015.
Siegenthaler et al., "Characterization and Expression of a Novel Human Fatty Acid-Binding Protein: The Epidermal Type {E-FABP}", Biochem Biophys Res Commun, vol. 190, pp. 482-487, 1993.
Sulsky et al., "Potent and selective biphenyl azole inhibitors of adipocyte fatty acid binding protein {aFABP}", Bioorganic & Medicinal Chemistry Letters, vol. 17, No. 12, pp. 3511-3515, 2007.
Tuncman et al., "A genetic variant at the fatty acid-binding protein aP2 locus reduces the risk for hypertriglyceridemia type 2 diabetes, and cardiovascular disease", PNAS, vol. 103, No. 18, pp. 6970-6975, 2006.
Van Der Fits et al., "Imiquimod-Induced Psoriasis-Like Skin Inflammation in Mice is Mediated via the IL-23/IL-17 Axis", The Journal of Immunology, vol. 182, No. 9, pp. 5836-5845, 2009.
Won et al., "Oligopeplide complex for targeted non-viral gene delivery to adipocytes", Nat Maler, vol. 13, pp. 1157-1164, 2014.
Wu et al., "Psoriasis induced by topical imiquimod", Australasian Journal of Dermatology, vol. 45, No. 1, pp. 47-50, 2004.
Yuspa et al., "Expression of Murine Epidermal Differentiation Markers is Tightly Regulated by Restricted Extracellular Calcium Concentrations In Vitro", J Cell Biol, vol. 109, pp. 1207-1217, 1989.
Zhou et al., "The discovery of novel and selective fatty acid binding protein 4 inhibitors by virtual screening and biological evaluation", Bioorganic & Medicinal Chemistry, vol. 24, No. 18, pp. 4310-4317, 2016.
Bolognia et al., Dermatology, 2012, Sounders, 3rd ed. {no copybook).
Chinese Office Action, for Application No. 2017000663567, issued Jul. 7, 2021, 5 pages, with English translation.
Kühne et al., Design and synthesis of selective, dual fatty acid binding protein 4 and 5 inhibitors, Bioorganic & Medicinal Chemistry Letters 26:5092-5097 (2016).
Lan et al., Small-molecule inhibitors of FABP4/5 ameliorate dyslipidemia but not insulin resistance in mice with diet-induced obesity, Journal of Lipid Research, 52:646-656 (2011).

\* cited by examiner

SEQUENCE LISTING

```
<160> NUMBER OF SEQ ID NOS: 9

<210> SEQ ID NO 1
<211> LENGTH: 646
<212> TYPE: DNA
<213> ORGANISM: Mus musculus
<220> FEATURE:
<221> NAME/KEY: misc_feature
<223> OTHER INFORMATION: FABP4

<400> SEQUENCE: 1
atagcaccct cctgtgctgc agcctttctc acctggaaga cagctcctcc tcgaaggttt      60
acaaaatgtg tgatgccttt gtgggaacct ggaagcttgt ctccagtgaa aacttcgatg     120
attacatgaa agaagtggga gtgggctttg ccacaaggaa agtggcaggc atggccaagc     180
ccaacatgat catcagcgta aatggggatt tggtcaccat ccggtcagag agtacttta      240 aaaacaccga gatttccttc aaactgggcg tggaattcga tgaaatcacc gcagacgaca     300
ggaaggtgaa gagcatcata accctagatg gcggggccct ggtgcaggtg cagaagtggg     360
atggaaagtc gaccacaata aagagaaaac gagatggtga caagctggtg gtggaatgtg     420
ttatgaaagg cgtgacttcc acaagagttt atgaaagggc atgagccaaa ggaagaggcc     480
tggatggaaa tttgcatcaa acactacaat agtcagtcgg atttattgtt ttttttaaa     540 gatatgattt tccactaata agcaagcaat taattttttc tgaagatgca ttttattgga     600
tatggttatg ttgattaaat aaaacctttt tagacttaga aaaaaa                    646

<210> SEQ ID NO 2
<211> LENGTH: 21
<212> TYPE: RNA
<213> ORGANISM: Homo sapiens

<400> SEQUENCE: 2
guagguaccu ggaaacuugu u                                                21
```

```
<210> SEQ ID NO 3
<211> LENGTH: 21
<212> TYPE: RNA
<213> ORGANISM: Homo sapiens

<400> SEQUENCE: 3
caaguuucca gguaccuacu u                                              21

<210> SEQ ID NO 4
<211> LENGTH: 21
<212> TYPE: RNA
<213> ORGANISM: Homo sapiens

<400> SEQUENCE: 4
gaaaugggau ggaaaaucau u                                              21

<210> SEQ ID NO 5
<211> LENGTH: 21
<212> TYPE: RNA
<213> ORGANISM: Homo sapiens

<400> SEQUENCE: 5
ugauuuucca ucccauuucu u                                              21

<210> SEQ ID NO 6
<211> LENGTH: 21
<212> TYPE: RNA
<213> ORGANISM: Homo sapiens

<400> SEQUENCE: 6
gaugugauca ccauuaaauu u                                              21

<210> SEQ ID NO 7
<211> LENGTH: 21
<212> TYPE: RNA
<213> ORGANISM: Homo sapiens

<400> SEQUENCE: 7
auuuaauggu gaucacaucu u                                              21

<210> SEQ ID NO 8
<211> LENGTH: 21
<212> TYPE: RNA
<213> ORGANISM: Homo sapiens

<400> SEQUENCE: 8
gaaagucaag agcaccauau u                                              21

<210> SEQ ID NO 9
<211> LENGTH: 21
<212> TYPE: RNA
<213> ORGANISM: Homo sapiens

<400> SEQUENCE: 9
uauggugcuc uugacuuucu u                                              21
```

FABP4 AS A THERAPEUTIC TARGET IN SKIN DISEASES

TECHNOLOGICAL FIELD

The present invention relates to methods of regulating proliferation and/or differentiation of keratinocytes and immune cells, more specifically to methods of treating pathologies characterized by hyperproliferative keratinocytes or inflammatory skin diseases.

BACKGROUND ART

References considered to be relevant as background to the presently disclosed subject matter are listed below:

[1] Furuhashi et al., Nat Rev Drug Discov 2008, 7(6), 489-503
[2] Coe et al., Biochim Biophys Acta 1998, 1391(3), 287-306
[3] Hotamisligil et al., Science 1996, 274(5291), 1377-1379
[4] Maeda et al., Cell Metab 2005, 1(2), 107-119
[5] Furuhashi et al., Nature 2007, 447(7147), 959-965
[6] Tuncman et al., PNAS 2006, 103(18), 6970-6975
[7] Garin-Shkolnik et al., Diabetes 2014, 63(3), 900-911
[8] Bolognia et al., Dermatology 2012, Sounders, $3^{rd}$ ed.
[9] Krueger et al., Annals of the Rheumatic Diseases 2005 (64), 30-36
[10] Siegenthaler et al., Biochem Biophys Res Commun 1993, 190, 482-487
[11] Floresta et al., Eur J Med Chem 2017, 138, 854-873
[12] Cao et al., Cell Metab 2013, 17, 768-778
[13] Burak et al., Sci Transl Med 2015, 7, 319ra205
[14] Miao et al., Mol Cell Endocrinol 2015, 403, 1-9
[15] Won et al., Nat Mater 2014, 13, 1157-1164
[16] Madsen et al., J Invest Dermatol 1992, 99(3), 299-305
[17] Guttman-Yassky et al., J Allergy Immunol 2011, 127(5), 1110-1118
[18] Yuspa et al., J Cell Biol 1989, 109, 1207-1217
[19] Wu et al., Australasian Journal of Dermatology 2004, 45(1), 47-50
[20] Van der Fits et al., The Journal of Immunology 2009, 182(9), 5836-5845

Acknowledgement of the above references herein is not to be inferred as meaning that these are in any way relevant to the patentability of the presently disclosed subject matter.

BACKGROUND

Fatty acid binding proteins (FABPs) are small cytoplasmic chaperones that serve as carriers of hydrophobic molecules, specifically long chain fatty acids and retinoic acid [1,2]. Several members of the FABP family have been identified as key regulators of various metabolic functions and have been linked to the development of insulin resistance, abnormal lipid metabolism, and atherosclerosis. FABPs shuttle intracellular fatty acids and other hydrophobic ligands to cellular destinations such as enzymes, membranes, and the nucleus. FABPs are also involved in modulating intracellular lipid metabolism and regulating gene expression.

Family members of the intracellular fatty acids chaperones are expressed in a tissue specific manner. FABP4, also termed A-FABP or aP2, is the major fatty acid binding protein in adipocytes and macrophages. Recent studies show that FABP4 is central to the pathway that links obesity to insulin resistance and plays an important role in systemic glucose and lipid metabolism [3,4]. FABP4 has proinflammatory properties in macrophages. An orally active small-molecule inhibitor of FABP4 was found to be an effective therapeutic agent against severe atherosclerosis and type 2 diabetes in mouse models [5]. Additionally, individuals that carry a T87C polymorphism of the FABP4 promoter, leading to a reduced transcriptional activity, have lower serum triglycerides and a significantly reduced risk of atherosclerosis and type 2 diabetes as compared with subjects carrying the homozygous WT allele [6].

The transcription factor peroxisome proliferator-activated receptor γ (PPARγ) is a master regulator of genes associated with adipogenesis, insulin responses and immune functions, with favorable outcomes following its activation. PPARγ has been suggested to decrease the inflammatory response of cardiovascular cells, specifically endothelial cells. It has been observed that FABP4 regulates PPARγ expression [7], whereby inhibition of FABP4 increased PPARγ levels in macrophages and adipocytes, and over-expression of FABP4 reduced PPARγ. It was also shown that FABP4 reduced PPARγ by triggering its ubiquitination and subsequent proteasomal degradation. In vivo, FABP4-null mouse pre-adipocytes exhibited increased expression of PPARγ and a remarkably enhanced adipogenesis compared to WT mice, indicating that FABP4 regulates the differentiation process. Obesity, mainly visceral obesity, increases morbidity and mortality by promoting insulin resistance, diabetes, and atherosclerosis. It was also found that FABP4 was increased and PPARγ was reduced in visceral fat in mice and humans, as compared to their levels in subcutaneous fat.

The skin functions as a mechanical barrier to the outside world, but it also uses the immune system for protection. Immune responses in the skin, however, are not always protective but can also be harmful in nature, and causing diseases [8]. Numerous skin diseases are caused by T lymphocytes and are therefore immunologically mediated. Consequently, many dermatoses respond favorably to immunosuppressive therapy administered either systemically or topically. Many of the dermatoses have a chronic course, and are therefore therapeutically challenging.

Psoriasis is a chronic inflammatory skin disease affecting approximately 2-4% of the world population. Its pathogenesis involves both epidermal and immunological functional defects. The hallmarks of psoriasis are abnormal differentiation and hyperproliferation of keratinocytes. In psoriasis, the infiltration of inflammatory cells and the activation of T lymphocytes lead to release of cytokines resulting in proliferation of keratinocytes and abnormal differentiation [9].

FABP5, FABP family member also known as epidermal and psoriasis-associated FABP, was previously found to be increased in psoriatic skin lesions [10]. However, the role of the metabolic regulator FABP4 in dermatologic diseases in general, and psoriasis in particular has yet to be observed.

General Description

The inventors of the invention described herein have discovered that FABP4 is an essential modulator in keratinocytes and immune cells for development of skin diseases, e.g. inflammatory skin diseases such as psoriasis. This enables the development of pharmaceutical agents and compositions that can be useful in inhibiting the development of skin diseases, and may be used to treat such diseases after they have developed.

Thus, in a first aspect of this disclosure, there is provided a pharmaceutical composition comprising at least one FABP4-inhibitor for use in treating or preventing a skin disease or condition in which FABP4 is involved.

The FABP4-inhibitor refers to an active agent, which effects FABP4 activity, either by decreasing, limiting, or blocking the action, function or expression of the FABP4 protein. Inhibition of FABP4 protein activity is to be understood in a broad sense, including range of inhibitory effects that FABP4-inhibitor may have on the normal (for example, uninhibited or control) protein activity. Inhibition of protein activity may, but need not, result in an increase in the level or activity of an indicator of the protein's activity (by way of example, this can happen when the protein of interest is acting as an inhibitor or suppressor of a downstream indicator). Thus, FABP4 protein activity may be inhibited when the level or activity of any direct or indirect indicator of the protein's activity is changed (for example, increased or decreased) by at least 10%, at least 20%, at least 30%, at least 50%, at least 80%, at least 100%, or at least 250% or more as compared to control measurements of the same indicator. Inhibition of protein activity may also be effected, for example, by inhibiting expression of the gene encoding the protein or by decreasing the half-life of the mRNA encoding the protein.

According to some embodiments, the FABP4-inhibitor may be selected from a peptide, an antibody, an antibody fragment, a small molecule, a small interfering RNA (siRNA), a small hairpin RNA (shRNA), and mixtures thereof.

The term small molecule is meant to denote molecules having a molecular weight of up to about 1000 Da (daltons), at times up to 500 Da.

The small molecule may be a chemical compound, having a ring as its main structural feature. The ring may be typically a 3- to 10-membered ring (more typically 5- to 6-membered ring) saturated or unsaturated (i.e. cycloalkyl or aryl), being fully carbonaceous or containing one or more hereoatoms. Namely, the main ring may be a cycloalkyl, a heterocyclyl, an aryl or a heteroaryl, wherein the heteroatom(s) are one or more of nitrogen, oxygen and sulphur. Alternatively, the small molecule may be a system of two or more fused rings or having a spiro conjugation, each of which being a cycloalkyl, a heterocyclyl, an aryl or a heteroaryl, each of the rings having 3- to 1O-ring atoms (more typically each having 5- or 6-ring atoms).

In other words, as used herein, cycloalkyl refers to a saturated mono- or multi-cyclic ring system, in certain embodiments of 3 to 10 carbon atoms, in other embodiments of 3 to 6 carbon atoms, in further embodiments in other embodiments of 5 or 6 carbon atoms; cycloalkenyl and cycloalkynyl refer to mono- or multicyclic ring systems that respectively include at least one double bond and at least one triple bond. The ring systems of the cycloalkyl, cycloalkenyl and cycloalkynyl groups may be composed of one ring or two or more rings which may be joined together in a fused, bridged or sprio-connected fashion. Cycloalk(en)(yn)yl refers to a cycloalkyl group containing at least one double bond and at least one triple bond. Heterocyclyl refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 4, of the atoms in the ring system is a heteroatom, that is, an element other than carbon, including but not limited to, nitrogen, oxygen or sulfur. In embodiments where the heteroatom(s) is(are) nitrogen, the nitrogen may be optionally substituted with alkyl, alkenyl, alkynyl, aryl, heteroaryl, aralkyl, heteroaralkyl, cycloalkyl, heterocyclyl, acyl, guanidine, or the nitrogen may be quaternized to form an ammonium group, each being further substituted.

As used herein, aryl refers to aromatic monocyclic or multicyclic groups containing from 5 to 10 carbon atoms. Aryl groups include, but are not limited to groups such as unsubstituted or substituted fluorenyl, unsubstituted or substituted phenyl, and unsubstituted or substituted naphthyl.

Heteroaryl refers to a monocyclic or multicyclic aromatic ring system, in certain embodiments, of 5 to 18 members where one or more, in one embodiment 1 to 4, of the atoms in the ring system is a heteroatom, that is, an element other than carbon, including but not limited to, nitrogen, oxygen or sulfur. The heteroaryl group may be optionally fused to an aromatic or non-aromatic ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

The main ring structure (either containing a single ring or being a fused multicyclic system), may be substituted on each of its possible substitution positions by a variety of substituents, e.g. an alkoxy or alkylthio group (RO- or RS- group), a halide (or halogen atom, namely I, Br, Cl and F), a pseudohalide (such as cyanide, cyanate, thiocyanate, selenocyanate, trifluoromethoxy, azide), a haloalkyl, a haloalkoxy, an ester (-COOR group), an ether (-R'OR group), an alkanoic acid (-ROOH), amino, sulphinyl (—S (O)—), sulphonyl (—S(O)$_2$—), sulpho (—S(O)$_2$O—), mono- or dialkylaminocarbonyl (—C(O)NHR or —C(O)NRR'), carboxamide (—NR'COR), amido (—C(O)NH—), thioamido (—C(S)NH—), oxyamido (—OC(O)NH—), thiaamido (—SC(O)NH—), dithiamido (—SC(S)NH—), ureido (—HNC(O)NH—), thioureido (—HNC(S)NH—), formamido (—NH—C(O)—H), and others.

wherein each of R and R' a $C_1$-$C_8$ straight or branched alkyl, alkylene, aryl or heteroaryl group.

Amino as used herein is meant to encompass primary, secondary or tertiary amines where the point of attachment is through the nitrogen atom which is substituted with $C_1$-$C_6$ straight or branched alkyl. In case of a tertiary amine, the substituent is the same or different.

In some embodiments, the small molecule may be selected from carbazole alkanoic acid or carbazole alkanoic acid derivatives, aryl sulfonamide or aryl sulfonamide derivatives, sulfonylthiophene or sulfonylthiophene derivatives, hydroxypyrimidine, carbazole or carbazole derivatives, indole or indole derivatives, carbazole or carbazole derivatives, benzoylbenzene or benzoylbenzene derivatives, biphenyl-alkanoic acid or biphenyl-alkanoic acid derivatives, oxazole-alkanoic acid or oxazole-alkanoic acid derivatives, pyrimidine or pyrimidine derivatives, pyrimidone or pyrimidone derivatives, pyridine or pyridine derivatives, pyrazine or pyrazine derivatives, pyrazinone or pyrazinone derivatives, tetrazole and tetrazole derivatives, triazolopyrimidine or triazolopyrimidine derivatives, triazolopyrimidinone or triazolopyrimidinone derivatives, pyrazole or pyrazole derivatives, (2-(2'-(5-ethyl-3,4-diphenyl-1H-pyrazol-1-yl)(1,1'-biphenyl)-3-yl)oxy)-acetic acid (BMS309403) and 4-{[2-methoxycarbonayl)-5-(2-thienyl)-3-thienyl]amino}-4-oxo-2-butanoic acid (BMS480404), and salts, stereomers, hydrates and mixtures thereof [11].

The term derivative refers to a chemically modified compound derived from a parent compound described herein, that differs from the parent compound by one or more elements, substituents and/or functional groups such that the derivative has the same or similar biological properties/activities as the parent compound, as defined herein. For example, a pyrazole derivative may be (2-(2'-(5-ethyl-3,4-diphenyl-1H-pyrazol-1-yl)(1,1'-biphenyl)-3-yl)oxy)-acetic acid (BMS309403).

The term alkanoic acid refers to acids of saturated or unsaturated carbon chains, containing from 1 (or 2) to 18 carbons, and are straight or branched, e.g. carboxylic, ethanoic, propanoic, butanoic, pentanoic, hexanoic, heptanoic, etc.

In other embodiments, the small molecule may be selected from carbazole butanoic acid, aryl sulfonamide, sulfonylthiophene or sulfonylthiophene derivatives, 4-hydroxypyrimidine, 2-hydroxypyrimidine, carbazole or carbazole derivatives, tetrahydrocarbazole or tetrahydrocarbazole derivatives, 2,3-dimethylindole or 2,3-dimethylindole derivatives, benzoylbenzene, biphenyl-alkanoic acid or biphenyl-alkanoic acid derivatives, 2-oxazole-alkanoic acid or 2-oxazole-alkanoic acid derivatives, tetrahydropyrimidine or tetrahydropyrimidine derivatives, pyridine or pyridine derivatives, pyrazine or pyrazinone derivatives, quinolone or quinolone derivatives, aryl carboxylic acid or aryl carboxylic acid derivatives, tetrazole, triazolopyrimidine or triazolopyrimidine derivatives, indole or indole derivatives, flavonoids (such as flavanoles, falvanones, isoflavone, pyrazole or pyrazole derivatives, (2-(2'-(5-ethyl-3,4-diphenyl-1H-pyrazol-1-yl)(1,1'-biphenyl)-3-yl)oxy)-acetic acid (BMS309403) and 4-{[2-methoxycarbonayl)-5-(2-thienyl)-3-thienyl]amino}-4-oxo-2-butanoic acid (BMS480404), and salts, stereomers, hydrates and mixtures thereof.

Exemplary small molecules which are FABP4 inhibitors are shown in Table 1.

TABLE 1

FABP4 inhibitors

1 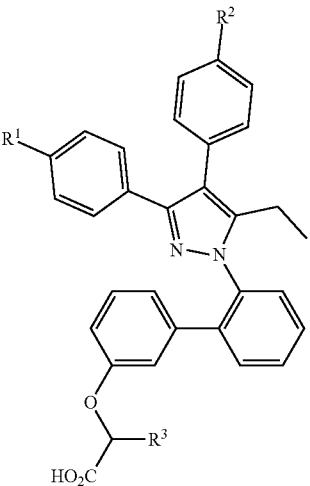

$R^1$, $R^2$ = H or halogen
$R^3$ = H, $C_{1-4}$-alkyl

2 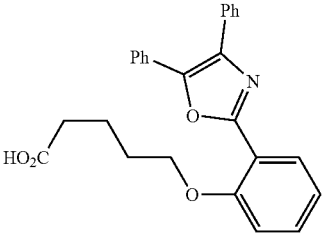 [SMILES: O=C(O)CCCCOc1ccccc1-c1nc(-c2ccccc2)c(-c2ccccc2)o1]

3 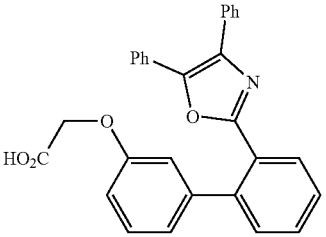 [SMILES: O=C(O)COc1cccc(-c2ccccc2-c2nc(-c3ccccc3)c(-c3ccccc3)o2)c1]

TABLE 1-continued
FABP4 inhibitors
| | | |
|---|---|---|
| 4 | 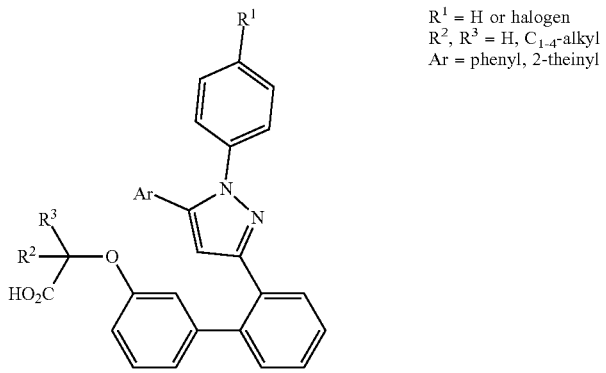 | $R^1$ = H or halogen<br>$R^2$, $R^3$ = H, $C_{1-4}$-alkyl<br>Ar = phenyl, 2-theinyl |
| 5 | 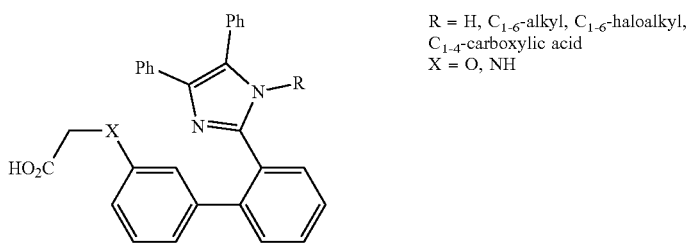 | R = H, $C_{1-6}$-alkyl, $C_{1-6}$-haloalkyl,<br>$C_{1-4}$-carboxylic acid<br>X = O, NH |
| 6 | 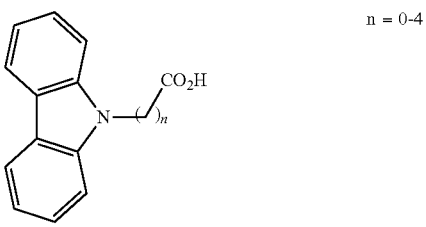 | n = 0-4 |
| 7 | 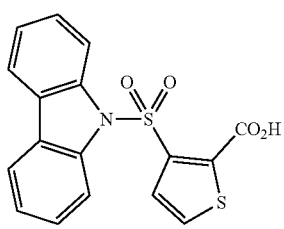 [SMILES: O=C(O)c1sccc1S(=O)(=O)n1c2ccccc2c2ccccc21] | |
| 8 | 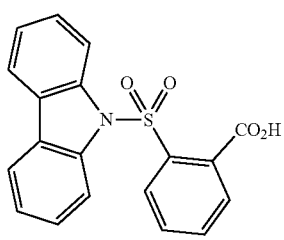 [SMILES: O=C(O)c1ccccc1S(=O)(=O)n1c2ccccc2c2ccccc21] | |
| 9 | 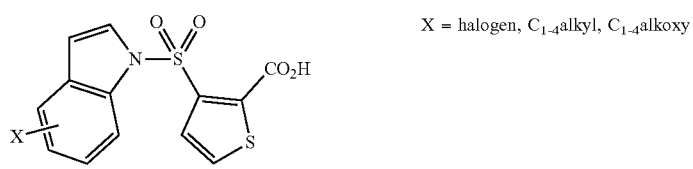 | X = halogen, $C_{1-4}$alkyl, $C_{1-4}$alkoxy |

TABLE 1-continued

FABP4 inhibitors

| | | |
|---|---|---|
| 10 | (structure: indole-N-sulfonyl-benzoic acid with X substituent) | X = halogen, $C_{1-4}$alkyl, $C_{1-4}$alkoxy |
| 11 | (structure: tetrahydrocarbazole with HO$_2$C at position 2 or 3, N-benzyl, ring size n) | n = 0-2 |
| 12 | (structure: 2,3-dimethyl-1-benzyl-indole-7-carboxylic acid) | |
| 13 | (structure: tetrahydrocarbazole with CO$_2$H, N-benzyl with R substituent, ring size n) | R = $C_{1-6}$-alkyl, $C_{1-4}$-haloalkyl, $C_{1-4}$-alkyl, CF$_3$, CONH$_2$, halogen<br>n = 1-2 |
| 14 | (structure: tetrahydrocarbazol-4-one/oxime with CO$_2$H, N-benzyl) | X = O, NOH |
| 15 | (structure: tetrahydrocarbazole with CO$_2$H, N-propyl, ring size n) | n = 1-2 |

TABLE 1-continued
FABP4 inhibitors
16 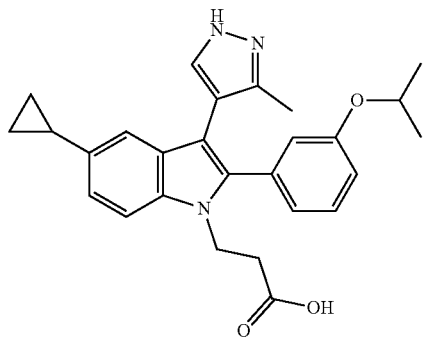 [SMILES: Cc1n[nH]cc1-c1c(-c2cccc(OC(C)C)c2)n(CCC(=O)O)c2ccc(C3CC3)cc12]
17 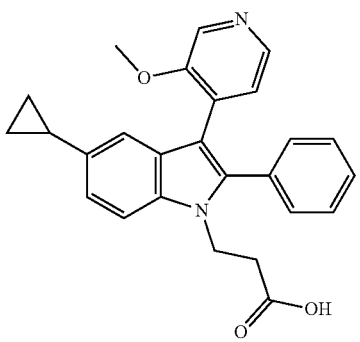 [SMILES: COc1cnccc1-c1c(-c2ccccc2)n(CCC(=O)O)c2ccc(C3CC3)cc12]
18 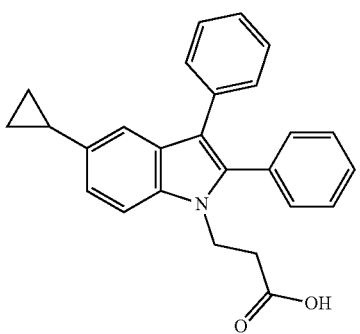 [SMILES: O=C(O)CCn1c(-c2ccccc2)c(-c2ccccc2)c2cc(C3CC3)ccc21]
19 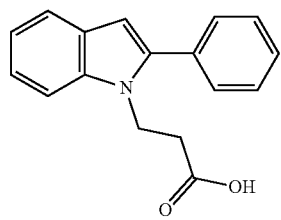 [SMILES: O=C(O)CCn1c(-c2ccccc2)cc2ccccc21]
20 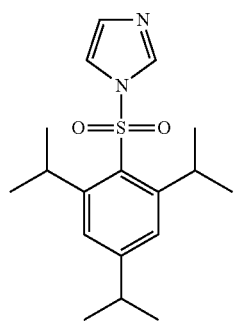 [SMILES: CC(C)c1cc(C(C)C)c(S(=O)(=O)n2ccnc2)c(C(C)C)c1]

TABLE 1-continued

FABP4 inhibitors

| | | |
|---|---|---|
| 21 | (structure: 5,6-disubstituted benzimidazole with R³, R², 2-R¹ substituents, N-sulfonyl linked to 2,4,6-triisopropylphenyl) | R¹ = H, C$_{1-4}$alkyl<br>R² = H, C$_{1-4}$alkyl, C$_{1-4}$alkoxy, halogen, NO$_2$, NH$_2$<br>R³ = H, C$_{1-4}$alkyl, C$_{1-4}$alkoxy, halogen, NO$_2$ |
| 22 | (structure: 2,4,6-triisopropylbenzenesulfonamide) | |
| 23 | (structure: 2,4,6-triisopropylbenzenesulfonic acid) | |
| 24 | (structure: 2,4,6-triisopropylbenzoic acid) | |
| 25 | (structure: methyl 5-(thiophen-2-yl)-4-[(E)-3-carboxyacryloylamino]thiophene-2-carboxylate) | |
| 26 | (structure: 4-hydroxy-6-(trifluoromethyl)-2-X-pyrimidine) | X = $-S-CH_2-C(=O)-N$(piperidine), |

TABLE 1-continued
FABP4 inhibitors
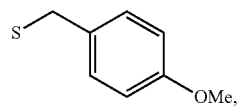
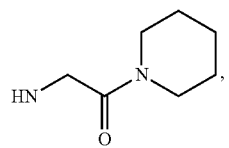
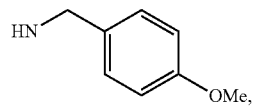
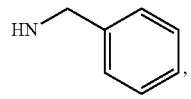
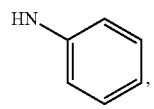
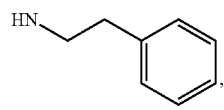
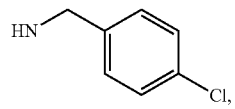
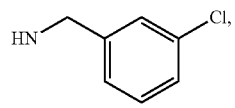
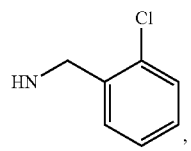
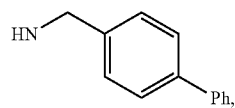
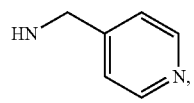
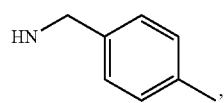
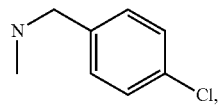

TABLE 1-continued
FABP4 inhibitors
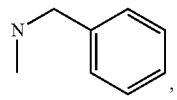,
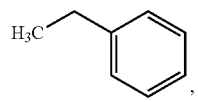,
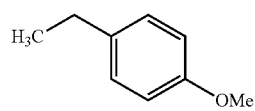
| | | |
|---|---|---|
| 27 | 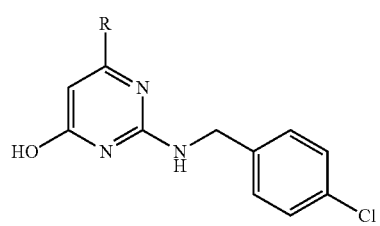 | R = C$_{1-4}$alkyl, phenyl, fluorophenyl |
| 28 | 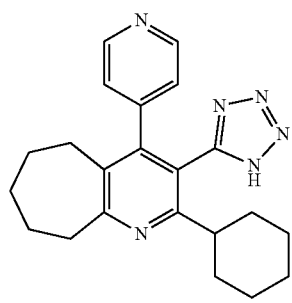 [SMILES: c1cc(-c2c3c(nc(C4CCCCC4)c2-c2nnn[nH]2)CCCCC3)ccn1] | |
| 29 | 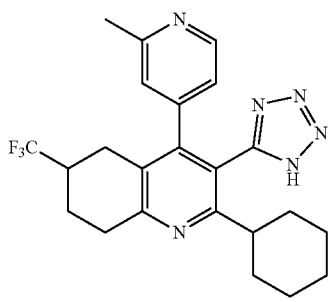 [SMILES: Cc1cc(-c2c3c(nc(C4CCCCC4)c2-c2nnn[nH]2)CCC(C(F)(F)F)C3)ccn1] | |
| 30 | 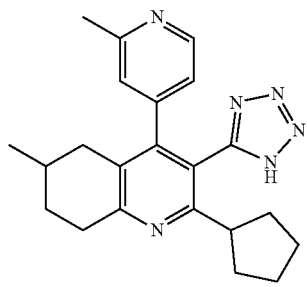 [SMILES: Cc1cc(-c2c3c(nc(C4CCCC4)c2-c2nnn[nH]2)CCC(C)C3)ccn1] | |

TABLE 1-continued
FABP4 inhibitors
31 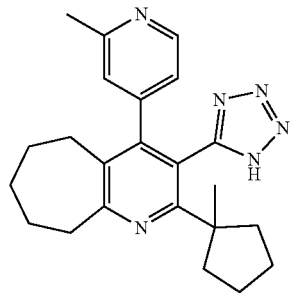 [SMILES: Cc1cc(-c2c3c(nc(C4(C)CCCC4)c2-c2nnn[nH]2)CCCCC3)ccn1]
32 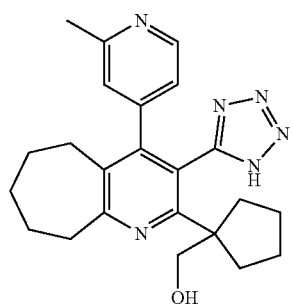 [SMILES: Cc1cc(-c2c3c(nc(C4(CO)CCCC4)c2-c2nnn[nH]2)CCCCC3)ccn1]
33 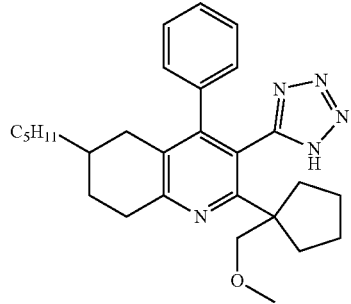
34 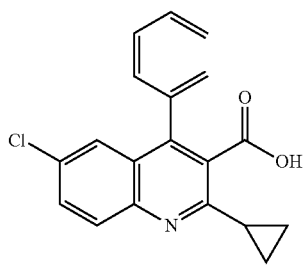 [SMILES: C=C/C=C\C(=C)c1c(C(=O)O)c(C2CC2)nc2ccc(Cl)cc12]
35 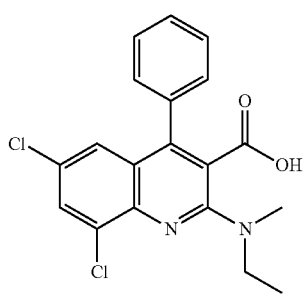 [SMILES: CCN(C)c1nc2c(Cl)cc(Cl)cc2c(-c2ccccc2)c1C(=O)O]

TABLE 1-continued
FABP4 inhibitors
36 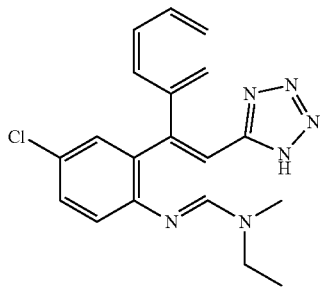 [SMILES: C=C/C=C\C(=C)/C(=C\c1nnn[nH]1)c1cc(Cl)ccc1/N=C/N(C)CC]
37 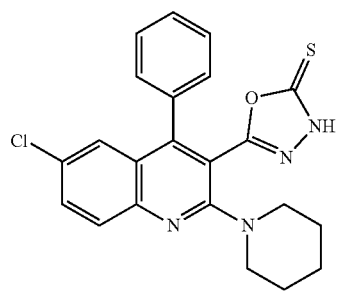 [SMILES: S=c1[nH]nc(-c2c(N3CCCCC3)nc3ccc(Cl)cc3c2-c2ccccc2)o1]
38 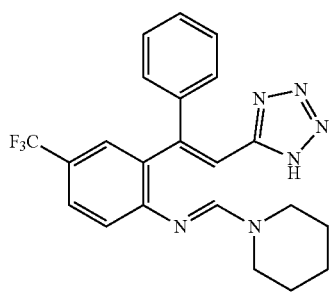 [SMILES: FC(F)(F)c1ccc(/N=C/N2CCCCC2)c(/C(=C/c2nnn[nH]2)c2ccccc2)c1]
39 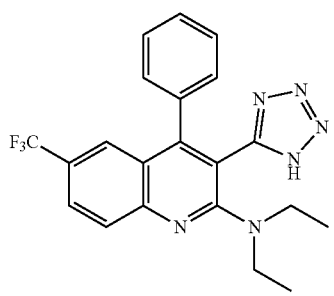 [SMILES: CCN(CC)c1nc2ccc(C(F)(F)F)cc2c(-c2ccccc2)c1-c1nnn[nH]1]
40 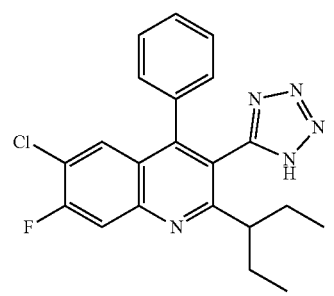 [SMILES: CCC(CC)c1nc2cc(F)c(Cl)cc2c(-c2ccccc2)c1-c1nnn[nH]1]

TABLE 1-continued
FABP4 inhibitors
41 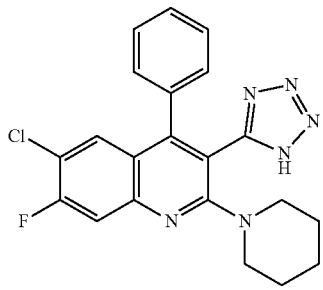 [SMILES: Fc1cc2nc(N3CCCCC3)c(-c3nnn[nH]3)c(-c3ccccc3)c2cc1Cl]
42 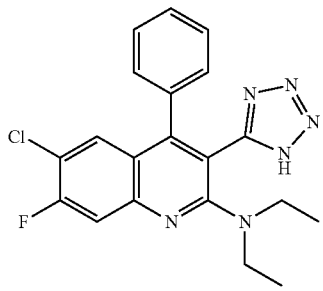
43 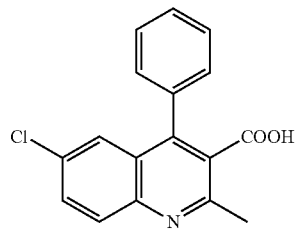 [SMILES: Cc1nc2ccc(Cl)cc2c(-c2ccccc2)c1C(=O)O]
44 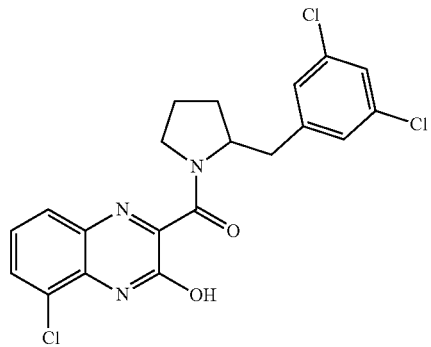 [SMILES: O=C(c1nc2cccc(Cl)c2nc1O)N1CCCC1Cc1cc(Cl)cc(Cl)c1]
45 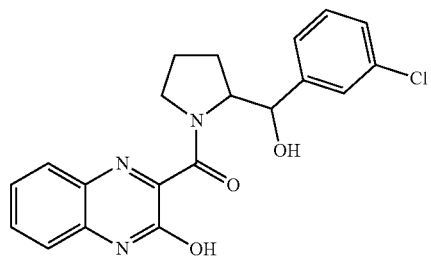 [SMILES: O=C(c1nc2ccccc2nc1O)N1CCCC1C(O)c1cccc(Cl)c1]

TABLE 1-continued
FABP4 inhibitors
46 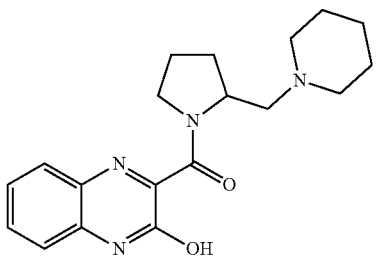 [SMILES: O=C(c1nc2ccccc2nc1O)N1CCCC1CN1CCCCC1]
47 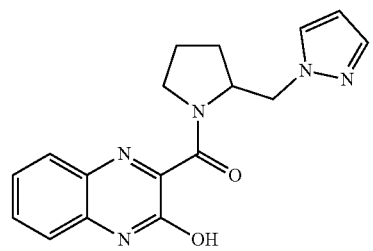 [SMILES: O=C(c1nc2ccccc2nc1O)N1CCCC1Cn1cccn1]
48 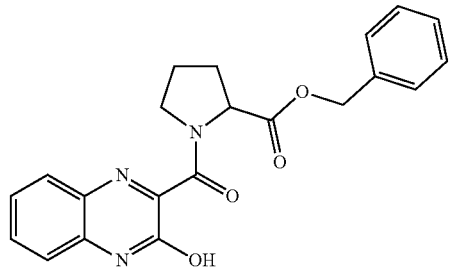 [SMILES: O=C(OCc1ccccc1)C1CCCN1C(=O)c1nc2ccccc2nc1O]
49 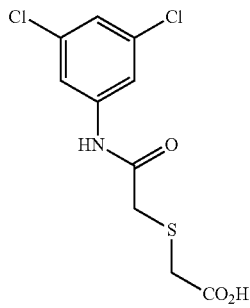 [SMILES: O=C(O)CSCC(=O)Nc1cc(Cl)cc(Cl)c1]
50 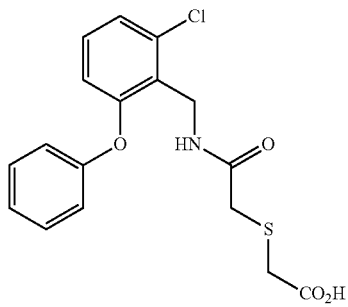 [SMILES: O=C(O)CSCC(=O)NCc1c(Cl)cccc1Oc1ccccc1]

TABLE 1-continued
FABP4 inhibitors
51 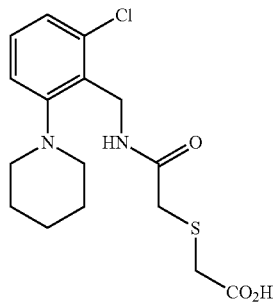 [SMILES: O=C(O)CSCC(=O)NCc1c(Cl)cccc1N1CCCCC1]
52 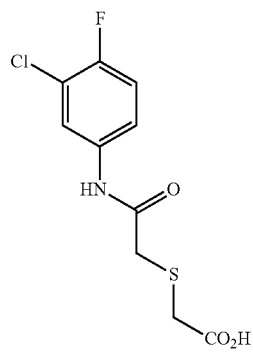 [SMILES: O=C(O)CSCC(=O)Nc1ccc(F)c(Cl)c1]
53 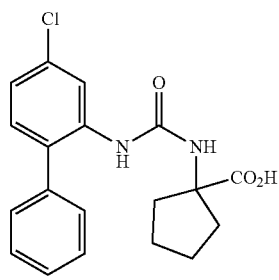 [SMILES: O=C(Nc1cc(Cl)ccc1-c1ccccc1)NC1(C(=O)O)CCCC1]
54 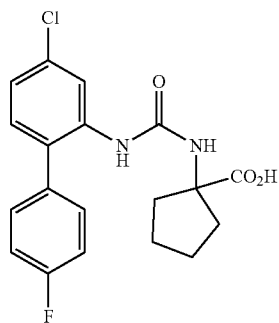 [SMILES: O=C(Nc1cc(Cl)ccc1-c1ccc(F)cc1)NC1(C(=O)O)CCCC1]
55 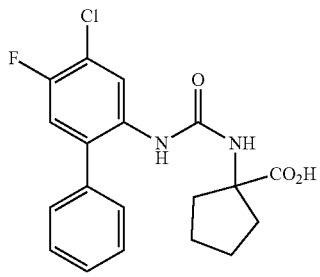 [SMILES: O=C(Nc1cc(Cl)c(F)cc1-c1ccccc1)NC1(C(=O)O)CCCC1]

TABLE 1-continued
FABP4 inhibitors
56 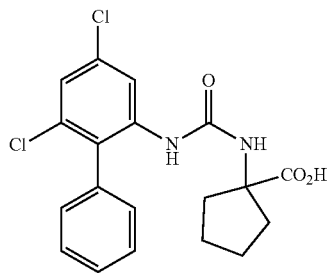 [SMILES: O=C(Nc1cc(Cl)cc(Cl)c1-c1ccccc1)NC1(C(=O)O)CCCC1]
57 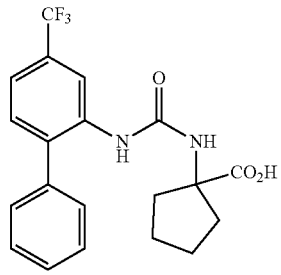 [SMILES: O=C(Nc1cc(C(F)(F)F)ccc1-c1ccccc1)NC1(C(=O)O)CCCC1]
58 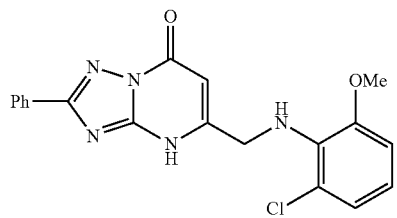 [SMILES: COc1cccc(Cl)c1NCc1cc(=O)n2nc(-c3ccccc3)nc2[nH]1]
59 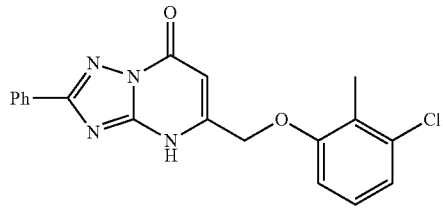 [SMILES: Cc1c(Cl)cccc1OCc1cc(=O)n2nc(-c3ccccc3)nc2[nH]1]
60 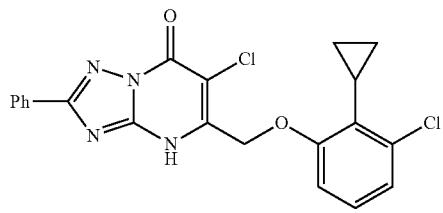 [SMILES: O=c1c(Cl)c(COc2cccc(Cl)c2C2CC2)[nH]c2nc(-c3ccccc3)nn12]
61 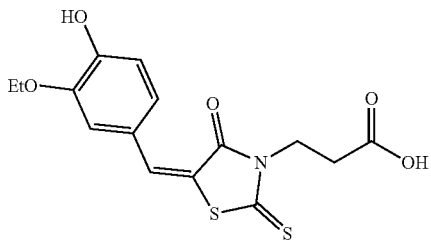 [SMILES: CCOc1cc(/C=C2/SC(=S)N(CCC(=O)O)C2=O)ccc1O]

TABLE 1-continued
FABP4 inhibitors
62 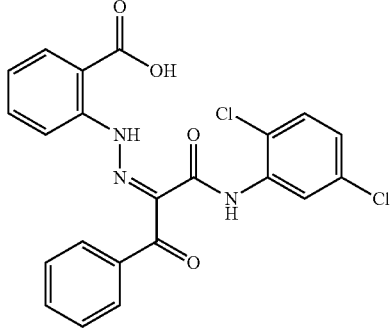 [SMILES: O=C(Nc1cc(Cl)ccc1Cl)/C(=N\Nc1ccccc1C(=O)O)C(=O)c1ccccc1]
63 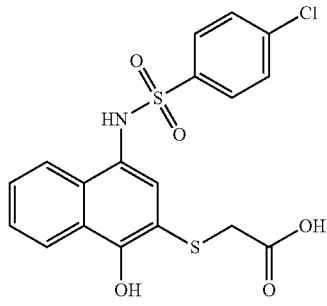 [SMILES: O=C(O)CSc1cc(NS(=O)(=O)c2ccc(Cl)cc2)c2ccccc2c1O]
64 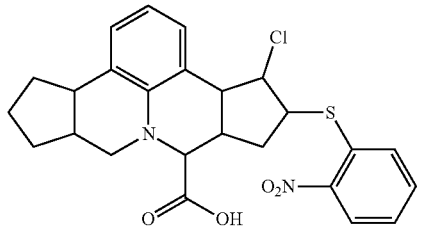 [SMILES: O=C(O)C1C2CC(Sc3ccccc3[N+](=O)[O-])C(Cl)C2c2cccc3c2N1CC1CCCC31]
65 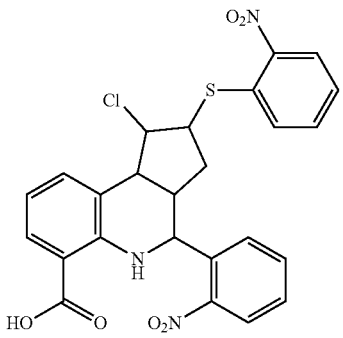 [SMILES: O=C(O)c1cccc2c1NC(c1ccccc1[N+](=O)[O-])C1CC(Sc3ccccc3[N+](=O)[O-])C(Cl)C21]
66 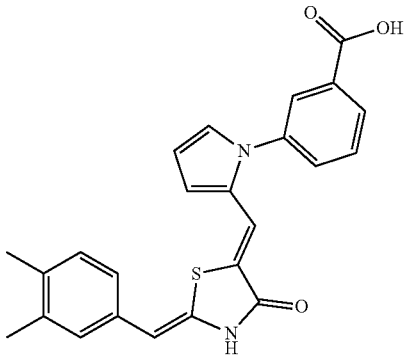 [SMILES: Cc1ccc(/C=c2/[nH]c(=O)/c(=C/c3cccn3-c3cccc(C(=O)O)c3)s2)cc1C]

TABLE 1-continued

FABP4 inhibitors

67 [Structure: 4-chloro-3-propoxyphenylsulfonamide linked to 4-carboxyphenyl]

68 [Polycyclic structure with carboxylic acid and two methyl groups]

69 [Polycyclic structure with carboxylic acid and Br substituent]

70 [Polycyclic structure with carboxylic acid and methyl substituent]

71 [Polycyclic structure with carboxylic acid and Cl substituent]

In some embodiments, the small molecule may be selected from those detailed in table 1.

In some embodiments, the small molecule may be at least one from those detailed in table 1.

In some other embodiments, the small molecule is selected from pyrazole or pyrazole derivatives, (2-(2'-(5-ethyl-3,4-diphenyl-1H-pyrazol-1-yl)(1,1'-biphenyl)-3-yl)oxy)-acetic acid (BMS309403) and 4-{[2-methoxycarbonayl)-5-(2-thienyl)-3-thienyl]amino}-4-oxo-2-butanoic acid (BMS480404), and salts, stereomers, hydrates and mixtures thereof.

In further embodiments, the small molecule may be (2-(2'-(5-ethyl-3,4-diphenyl-1l1-pyrazol-1-yl)(1,1'-biphe- nyl)-3-yl)oxy)-acetic acid (BMS309403). In some other embodiments, the small molecule may be 4-{[2-methoxycarbonayl)-5-(2-thienyl)-3-thienyl]amino}-4-oxo-2-butanoic acid (BMS480404).

The FABP4-inhibitor, by some embodiments, may be an antibody that specifically binds to and inhibits the activity of FABP4. The antibody is a polypeptide ligand comprising at least a light chain or a heavy chain immunoglobulin variable region, which specifically recognizes and binds an epitope of an antigen, namely to a FABP4 protein or a fragment thereof. The term means to denote intact immunoglobulins and their variants and portions known in the art, such as Fab' fragments, F(ab)'₂ fragments, single chain Fv proteins ("scFv"), and disulfide stabilized Fv proteins ("dsFv"). The term also includes recombinant forms such as chimeric antibodies (for example, humanized murine antibodies), and heretoconjugate antibodies (such as, bispecific antibodies). See also, Pierce Catalog and Handbook, 1994-1995 (Pierce Chemical Co., Rockford, IL); Kuby, Immunology, 3rd Ed., W. H. Freeman & Co., New York, 1997.

The antibody may be a monoclonal antibody or a polyclonal antibody. Monoclonal antibodies are produced by a single clone of B-lymphocytes or by a cell into which the light and heavy chain genes of a single antibody have been transfected, including humanized monoclonal antibodies. Polyclonal antibodies are antibodies that are secreted by different B cell lineages within the body.

The antibodies are said to bind specifically to FABP4 protein or fragments thereof; namely, the antibodies are capable of associating in a selective and preferable manner with FABP4 proteins or their fragments, over binding with other molecular/macromolecular entities with which FABP4 proteins and their fragments are admixed. An antibody having inhibitory effect (or neutralizing effect) on FABP4 is an antibody that inhibits or suppresses at least one activity of FABP4 or at least one activity associated with FABP4; for example, by blocking the binding of FAPB4 to a ligand to which it normally binds, by disrupting or otherwise interfering with a protein-protein interaction of the FABP4 with another protein, etc.

In some embodiments, the antibody is an anti-FABP4 antibody. Exemplary anti-FABP4 antibodies are described in the art, and may include, inter alia, Ab anti FABP4 [12], Ab CA33 [13], Ab 2E4 [14], and others.

The FABP4-inhibitor may, by some embodiments, be an antisense or a sense inhibitor. Antisense and sense inhibitors are bio-macromolecules that bind (or hybridize) with messenger RNA (mRNA) produced by specific genes, e.g. FABP4 encoding gene, and inactivate or modulate their expression. The antisense inhibitor is typically an oligomeric compound that is at least partially complementary to the region of a specific target nucleic acid molecule to which it hybridizes, thus causing RNA interference (RNAi). Thus, RNAi works through the targeting of mRNA via sequence-specific matches and results in degradation of target mRNA or its translational inhibition, leading to altering or loss of protein expression, for example suppression of expression of FABP4. Non-limiting examples of antisense compounds include primers, probes, antisense oligonucleotides, siRNAs, miRNAs, shRNA and ribozymes. Either an antisense or a sense inhibitor can be used to target a portion of dsDNA, as both will interfere with the expression of that portion of the dsDNA. The antisense molecule can bind to the plus strand, and the sense molecule can bind to the minus strand. These compounds can be introduced as single-stranded, double-stranded, circular, branches or hairpin compounds and can contain structural elements such as internal or terminal bulges or loops. Double-stranded antisense compounds can be two strands hybridized to form double-stranded compounds or a single strand with sufficient self-complementarity to allow for hybridization and formation of a fully or partially double-stranded compound.

The FABP4-inhibitor may be small interfering RNA (siRNA), which are small 19-25 bp dsRNA molecules, with phosphorylated 5' ends and hydroxylated 3' ends, with two overhanging nucleotides. An example of specific interfering RNA delivery into adipose tissue against cell type-specific carrier molecules is described in [15] (incorporated herein by reference). In some embodiments, the FABP4-inhibitor is an siRNA comprising the nucleic acid sequences SEQ ID NO: 2-9:

```
sense
                                  (SEQ ID NO: 2)
   3' guagguaccuggaaacuuguu antisense
                                  (SEQ ID NO: 3)
   5' caaguuuccagguaccuacuu sense
                                  (SEQ ID NO: 4)
   3' gaaaugggauggaaaaucauu antisense
                                  (SEQ ID NO: 5)
   5' ugauuuuccaucccauuucuu sense
                                  (SEQ ID NO: 6)
   3' gaugugaucaccauuaaauuu antisense
                                  (SEQ ID NO: 7)
   5' auuuaauggugaucacaucuu sense
                                  (SEQ ID NO: 8)
   3' gaaagucaagagcaccauauu antisense
                                  (SEQ ID NO: 9)
   5' uauggugcucuugacuuucuu.
```

It is of note that selecting suitable FABP4-inhibitors may be carried out by any suitable method known per-se (see, for example Hughes et al., Br J Pharmacol. 2011, 162(6), 1239-1249). For example, active compounds may be selected from libraries and screened, based on their selectivity to FABP4 and their resulting potency or activity towards FABP4 inhibition.

As further noted above, it has been previously observed by the inventors of the present invention that PPARγ expression in macrophages and adipocytes is negatively regulated by FABP4, and that FABP4 was increased and PPARγ was reduced in inflammatory sites such as the visceral fat [7]. The inventors have now found that FABP4 is overexpressed in skin, in T lymphocytes and keratinocytes, and that there is a negative correlation between FABP4 and PPARγ expression there as well, for example in inflammation-involved skin. Therefore, without wishing to be bound by theory, the inhibition of FABP4 concomitantly with activation of PPARγ may have a synergistic effect in treating various skin diseases.

Thus, the pharmaceutical compositions of this disclosure may comprise, or used concomitantly with, at least one PPARγ agonist. The PPARγ agonist is an active agent which binds to the peroxisome proliferator-activated receptor, and activates the receptor.

According to some embodiments, the pharmaceutical composition may comprise at least one PPARγ agonist. In some embodiments, the at least one PPARγ agonist is a thiazolidinedione derivative. In other embodiments, the PPARγ agonist may be selected from Pioglitazone (Actos), Rosiglitazone (Avandia), Lobeglitazone (Duvie), Ciglitazone, Darglitazone, Englitazone, Netoglitazone, Rivoglitazone, Troglitazone (Rezulin), Rhodanine, and other thiazolidinedione derivatives. As a man of the art would appreciate, other PPARγ agonists are also encompassed by the scope of the present disclosure, such as indole-derivatives or various non-steroidal anti-inflammatory drugs (e.g. ibuprofen), as well as other PPARγ agonists.

The pharmaceutical compositions of this disclosure may comprise a pharmaceutically acceptable carrier. The pharmaceutically acceptable carrier may be for example, vehicles, adjuvants, excipients, or diluents, and are well-known to those who are skilled in the art and are readily available to the public. See, for example, Remington's Pharmaceutical Science, by E. W. Martin, Mack Publishing Co., Easton, PA, 15th Edition (1975). It is preferred that the pharmaceutically acceptable carrier be one which is chemically inert to the active compounds and one which has no detrimental side effects or toxicity under the conditions of use. The choice of carrier will be determined in part by the particular active agent, as well as by the particular method used to administer the composition. Accordingly, there is a wide variety of suitable formulations of the pharmaceutical composition encompassed by the present disclosure.

The pharmaceutically acceptable carriers may be suitable for topical, oral, rectal, vaginal, transdermal, subcutaneous, intravenous, intramuscular, ocular, and intranasal administration of the FABP4-inhibitor. The pharmaceutical compositions are prepared in a manner well known in the pharmaceutical art. In making the pharmaceutical compositions of this disclosure, the components are usually mixed with an excipient, diluted by an excipient or enclosed within such a carrier which can be manipulated to the desired form. Based on the particular mode of administration, the pharmaceutical composition may be formulated into tablets, pills, capsules, sachets, granules, powders, chewing gum, suspensions, emulsions, solutions, gels, lotions, oils, soaps, sprays, creams, ointments, films, microcapsules, microspheres, liposomes, vesicles, microemulsions, liposheres, patches, and ethosomes.

The pharmaceutical composition may, by some embodiments, be adapted for delivery of the at least one FABP4-inhibitor topically, orally, by inhalation, nasally, transdermally, ocularly or parenterally into the circulatory system of a subject.

According to some embodiments, the pharmaceutical compositions are adapted for administration of said at least one FABP4-inhibitor by injection.

According to other embodiments, the pharmaceutical compositions are adapted for oral administration of said at least one FABP4-inhibitor.

Formulations suitable for oral administration can consist of (a) liquid solutions, such as an effective amount of the compound, or composition comprising same, dissolved in diluents, such as water, saline, or juice (e.g. orange juice); (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, preservatives, flavoring agents, and pharmacologically compatible carriers. Lozenge forms can comprise the active ingredient in a flavor, usually sucrose and acacia or tragacanth, as well as pastilles comprising the active formulation in an inert base, such as gelatin and glycerin, or sucrose and acacia, emulsions, gels, and the like containing, in addition to the active formulation, such carriers as are known in the art.

The pharmaceutical compositions of this disclosure, being for use in treating or preventing an inflammatory skin disease, may be adapted to induce a systemic or a non-systemic effect; namely, the compositions may be adapted to deliver the active agent, FABP4-inhibitor, into the circulatory system of a subject, or to deliver the active agent to a target site (e.g. a specific layer of the skin).

As known, human skin is made of numerous layers which may be divided into three main group layers: Stratum corneum which is located on the outer surface of the skin, the epidermis, and the dermis. While the Stratum corneum is a keratin-filled layer of cells in an extracellular lipid-rich matrix, which in fact is the main barrier to drug delivery into skin, the epidermis and the dermis layers are viable tissues. The epidermis is free from blood vessels, but the dermis contains capillary loops that can channel therapeutics for transepithelial systemic distribution.

In some embodiments, the pharmaceutical composition is adapted for transdermal administration of said at least one FABP4-inhibitor. In other embodiments, the pharmaceutical compositions are adapted for topical administration of said at least one FABP4-inhibitor across skin layers. In some other embodiments, the pharmaceutical compositions are adapted for topical delivery of said at least one FABP-inhibitor across the Stratum corneum.

The pharmaceutical compositions may be formulated in any form suitable for dermal or topical administration, such as a gel, a lotion, oil, soap, a spray, an emulsion, a cream, an ointment, a solution, a suspension, a film, microcapsules, microspheres, liposomes, vesicles, microemulsions, liposheres, and patches.

The pharmaceutical compositions of this disclosure are used for treating or preventing a skin disease or condition in which FABP4 is overexpressed. In some embodiments, the skin disease or condition may be selected from the group consisting of psoriasis, dermatitis (atopic, seborrheic, contact), eczema, parapsoriasis, lichen planus, lichen plano-pilaris, *pityriasis* lichenoides et varioliformis *acuta*, *pityriasis* lichenoides chronica, *pityriasis rubra* pilaris, *pityriasis rosea*, graft-versus-host disease, histiocytoses, drug-induced eruptions, autoimmune connective tissue diseases (e.g. lupus), rosacea, folliculitis, acne, warts, ichthyosis, vitiligo, scarring alopecia, cutaneous T cell lymphoma (CTCL), actinic keratosis, squamous cell carcinoma, basal cell carcinoma, nevus, lichen simplex chronicus, xerosis, keratosis, keratoderma, pruritus, a burn, a scar, a callus, and a keloid.

According to some embodiments, the skin disease is lymphoma (CTCL).

In other embodiments, the pharmaceutical compositions of this disclosure are used for treating or preventing an inflammatory skin disease or condition. Namely, the compositions cause at least one therapeutic effect on skin diseases or conditions that involve an inflammatory component in which FABP4 is overexpressed.

In some embodiments, the inflammatory skin disease or condition may be selected from the group consisting of psoriasis, dermatitis (atopic, seborrheic, contact), eczema, parapsoriasis, lichen planus, lichen plano-pilaris, *pityriasis* lichenoides et varioliformis *acuta,* *pityriasis* lichenoides chronica, *pityriasis rubra* pilaris, *pityriasis rosea*, graftversus-host disease, histiocytoses, drug-induced eruptions, autoimmune connective tissue diseases (e.g. lupus), rosacea, folliculitis, acne, warts, ichthyosis, vitiligo, scarring alopecia, and CTCL.

According to such embodiments, the inflammatory skin disease is psoriasis. According to other embodiments, the inflammatory skin disease is dermatitis (atopic, seborrheic, contact).

According to another aspect, there is provided a topical formulation for transdermal delivery of at least one FABP4-inhibitor, said composition comprising at least one FABP4-inhibitor and at least one pharmaceutically acceptable carrier. In some embodiments, the topical formulation may further comprise at least one PPARγ agonist.

A further aspect of the present disclosure provides a method for treating or preventing a skin disease in a subject (e.g. an inflammatory skin condition), comprising administering to a subject in need thereof, a therapeutically effective amount of at least one FABP4-inhibitor or a pharmaceutical composition comprising thereof. The FABP4-inhibitors for use in the method of treatment may be selected from those detailed herein.

In a further aspect, there is provided a method for treating or preventing psoriasis in a subject, comprising administering to a subject in need thereof, a therapeutically effective amount of at least one FABP4-inhibitor or a pharmaceutical composition comprising thereof.

Another aspect provides a method for treating or preventing CTCL in a subject, comprising administering to a subject in need thereof, a therapeutically effective amount of at least one FABP4-inhibitor or a pharmaceutical composition comprising thereof.

The pharmaceutical compositions of this disclosure may be selected to treat, prevent or diagnose any pathology or condition. The term treatment or any lingual variation thereof, as used herein, refers to the administering of a therapeutic amount of the FABP4-inhibitor of composition comprising thereof, which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

As known, the effective amount for purposes herein may be determined by such considerations as known in the art. The amount must be effective to achieve the desired therapeutic effect, depending, inter alia, on the type and severity of the disease to be treated and the treatment regimen. The effective amount is typically determined in appropriately designed clinical trials (dose range studies) and the person versed in the art will know how to properly conduct such trials in order to determine the effective amount. As generally known, the effective amount depends on a variety of factors including the affinity of the ligand to the receptor, its distribution profile within the body, a variety of pharmacological parameters such as half-life in the body, on undesired side effects, if any, on factors such as age and gender, and others.

The method of treatment, according to some embodiments, may further comprise administering a PPARγ agonist to the subject. PPARγ agonist may be administered concomitantly with said at least one FABP4-inhibitor, or sequentially to the FABP4-inhibitor.

As used herein, concomitantly (or simultaneously) or any lingual variation thereof is used to mean that the components of a composition are administered concurrently, e.g., one together with the other. Simultaneous administration may permit one component in the combination to be administered within a certain time period (e.g., 5 minutes, 10 minutes or even a few hours) after the other, provided that the circulatory half-life concentration of the first administered component in a combination is concurrently present in therapeutically effective amounts with the other components administered thereafter. The time delay between administration of the components may vary depending on the exact nature of the components and the formulation containing them, the interaction between the individual components, their respective half-lives, and on such other factors as easily recognized by the versed artesian.

Sequentially (or separately) or any lingual variation thereof is used herein to mean that the time period between administering one component and the other is significant i.e., the first administered component may no longer be present (or is present in subclinical amounts) in the bloodstream in a therapeutically effective amount when the second (or subsequent) component is administered.

As noted above, it was discovered by the inventors that FABP4 is overexpressed in keratinocytes or inflammatory cells (such as macrophages, and lymphocytes) in a skin tissue biopsy from patients with inflammatory skin disease, but is not significantly expressed in non-involved skin tissue. Accordingly, identification of FABP4 overexpression can be utilized to detect early onset inflammatory skin disorders or detect predisposition of a subject to develop an inflammatory skin disease.

Thus, another aspect of the present disclosure provides a method for detecting the predisposition in a subject for developing an inflammatory skin disease or condition (or detect early onset of said inflammatory skin disease or condition), the method comprises detecting expression of FABP4 in a sample containing keratinocytes or inflammatory cells from the subject, wherein the presence of FABP4 in the sample above a pre-determined base-level indicates a predisposition for developing the inflammatory skin disease or condition. The inflammatory skin disease or condition may be any of the diseases and conditions described herein.

In some embodiments, said pre-determined base-level is a level of FABP4 in a normal skin sample The term predisposition refers herein to an effect of a factor or factors that render a subject susceptible to a condition, disease, or disorder, such as an inflammatory skin disease. In some embodiments, the disclosed methods may be used to identify a subject predisposed to developing a condition, disease, or disorder.

It is to be understood that detection may be qualitative or quantitative, and may be carried out by any suitable method known per-se; non-limiting examples of such methods may be immunohistochemistry, PCR techniques (including RT-PCT and qRT-PCR), Western analysis, in-situ hybridization, and others.

The biological sample may be obtained directly or indirectly from the subject, including whole blood, plasma, serum, tears, mucus, saliva, urine, pleural fluid, tissues, cells (such as fibroblasts, peripheral blood mononuclear cells, or skin cells), organs, and/or extracts of tissues.

In some embodiments, the biological sample is a skin sample.

It is to be understood that detection of FABP4 in the sample may refer to detecting the expression of a FABP4 nucleic acid, expression of a FABP4 protein fragment, and/or expression of a FABP4 protein.

The control level or base-level refers to a reference standard, such as a known value indicative of base concentration or expression of FABP4 in a healthy subject or from a non-involved sample of the subject. In particular examples a control sample is taken from a subject that is known not to have a disease or condition, such as psoriasis. In other examples a control is taken from the subject being diagnosed, but at an earlier time point, either before disease onset or prior to or at an earlier time point in disease treatment.

The difference between a test sample and a control can be an increase or conversely a decrease of expression of FABP4 protein, fragment or nucleic acid. The difference can be a qualitative difference or a quantitative difference, for example a statistically significant difference. In some examples, a different is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or greater than 500%.

In yet another aspect, the present disclosure provides a method for treating or preventing an inflammatory skin disease in a subject, comprising:
- detecting expression of FABP4 in a sample containing keratinocytes or inflammatory cells from the subject,
- determining whether FABP4 expression is above or below a pre-determined base-level, and
- administering to the subject a therapeutically effective amount of at least one FABP4-inhibitor or a pharmaceutical composition comprising thereof if the FABP4 expression in the sample is above said pre-determined base-level.

The subject to be treated or diagnosed refers to both human and non-human mammals (i.e. both human and veterinary subjects, for example, humans, non-human primates, dogs, cats, horses, and cows).

As used herein, the singular form "a", "an" and "the" include plural references unless the context clearly dictates otherwise.

As used herein, the term about is meant to encompass deviation of ±10% from the specifically mentioned value of a parameter, such as concentration, molecular weight, etc.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DESCRIBED SEQUENCES

The nucleic acid sequences provided herewith (Table 2 below) are shown using standard letter abbreviations for nucleotide bases as defined in 37 C.F.R. 1.822. Only one strand of each nucleic acid sequence is shown, but the complementary strand is understood as included by any reference to the displayed strand.

TABLE 2

Sequence listing

| SEQ ID NO: | | |
|---|---|---|
| 1 (cDNA sequence of mouse FABP4 that was inserted into a lentiviral vector) | atagcaccct acctggaaga acaaaatgtg ggaagcttgt attacatgaa ccacaaggaa ccaacatgat tggtcaccat aaaacaccga tggaattcga ggaaggtgaa gcggggccct atggaaagtc gagatggtga ttatgaaagg atgaaagggc tggatggaaa agtcagtcgg gatatgattt taattttttc tatggttatg tagacttaga | cctgtgctgc cagctcctcc tgatgccttt ctccagtgaa agaagtggga agtggcaggc catcagcgta ccggtcagag gatttccttc tgaaatcacc gagcatcata ggtgcaggtg gaccacaata caagctggtg cgtgacttcc atgagccaaa tttgcatcaa atttattgtt tccactaata tgaagatgca ttgattaant aaaaaa | agcctttctc tcgaaggttt gtgggaacct aacttcgatg gtgggctttg atggccaagc aatgggatt agtacttta aaactgggcg gcagacgaca accctagatg cagaagtggg aagagaaaac gtggaatgtg acaagagttt ggaagaggcc acactacaat tttttttaaa agcaagcaat ttttattgga aaaaccttt |
| 2 | sense | 3'-N guagguaccuggaaacuuguu |
| 3 | anti-sense | 5'-P caaguuuccagguaccuacuu |
| 4 | sense | 3'-N gaaauggauggaaaaucauu |
| 5 | anti-sense | 5'-P ugauuuccaucccauuucuu |
| 6 | sense | 3'-N gaugugaucaccauuaaauuu |
| 7 | anti-sense | 5'-P auuuaauggugaucacaucuu |
| 8 | sense | 3'-N gaaagucaagagcaccauauu |
| 9 | anti-sense | 5'-P uauggugcucuugacuuucuu |

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The following examples are provided to illustrate certain particular features and/or embodiments. These examples should not be construed to limit the disclosure to the particular features or embodiments described.

Example 1: Tissue Expression Analysis of FABP4, FABP5, and PPARγ in Human Psoriatic Skin Lesions Punch biopsies (4 mm in diameter) were obtained from disease-involved skin of patients with psoriasis (n=10). Biopsies were further obtained from involved skin of patients with chronic dermatitis (n=5). Normal skin was obtained from patients after surgical reduction of redundant skin (n=10). The tissues were fixed in formalin and embedded in paraffin. For histopathological examination with light microscopy, the sections were stained with hematoxylin and eosin (H&E) and observed by a pathologist who confirmed the diagnosis. In addition, for immunohistochemical analysis, the sections were stained with the following antibodies: FABP4 (Rabbit polyclonal anti FABP4 antibody, PAB12276, Abnova), FABP5 (Rabbit polyclonal anti FABP5 antibody, SC-50379, Santa Crus) and PPARγ (mouse monoclonal anti-PPARγ antibody, E-8, Santa Crus), all diluted 1:50. The paraffin-embedded and cryopreserved tissues were processed according to a standard protocol.

Figure 1A:
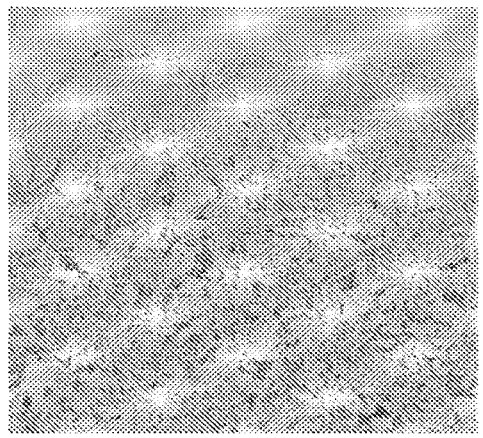
FIGS. 1A-1F show expression of FABP4 and PPARγ proteins in immunohistochemistry staining of human skin: healthy controls skin (FIGS. 1A-1B), psoriasis-involved skin (FIGS. 1C-1D), and dermatitis-involved skin (FIGS. 1E-1F). Tissue sections were stained with anti FABP4 (FIGS. 1A, 1C, 1E) or anti PPARγ (FIGS. 1B, 1D, 1F) antibodies. Original magnification ×100.
Figure 1B:
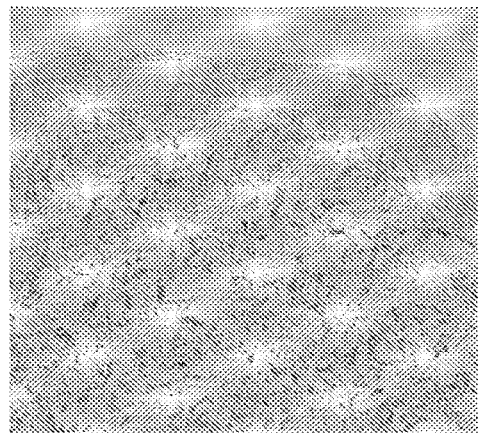
Figure 1C:
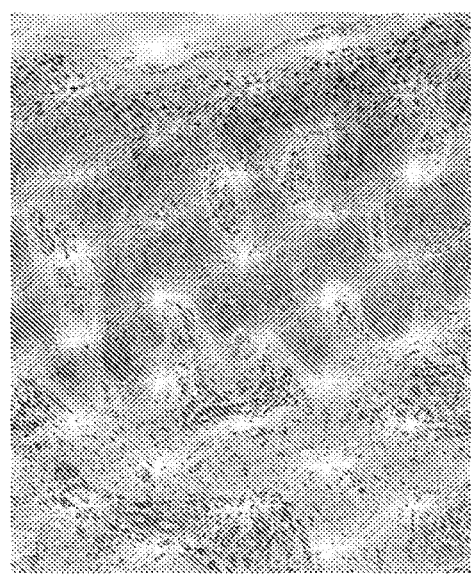

FIG. 1C shows high expression levels of FABP4 as detected in psoriatic skin lesions compared to normal skin (FIG. 1A), both in the epidermis and the dermis. This finding was observed in all the psoriasis-involved biopsies that were tested (100 percent prevalence). To the best of the inventors' knowledge, this is the first time that the expression of FABP4 in keratinocytes and dermal cells in psoriatic lesions has been reported. Without wishing to be bound by theory, this finding may suggest that FABP4 overexpression is related to the dysregulation of keratinocyte proliferation and differentiation in psoriasis. In addition, this observation supports a role of FABP4 in promoting inflammation by its action in dermal immune cells, which is another significant feature of psoriasis.

Figure 1D:
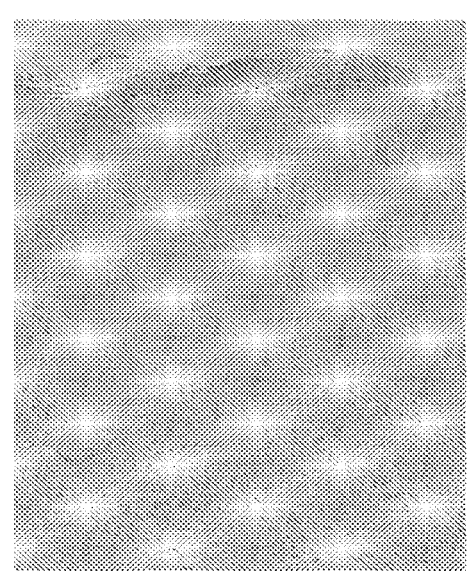
Figure 1E:
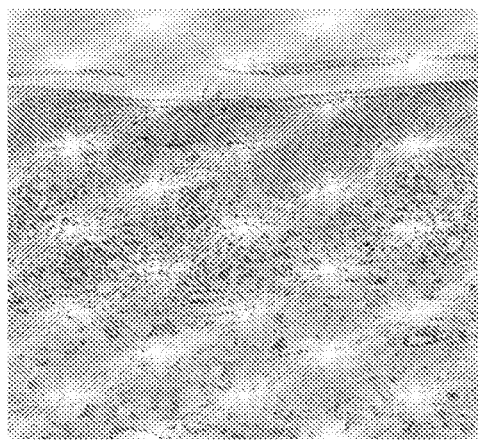

Increased level of FABP4 in both keratinocytes and inflammatory cells in the dermis were also observed in skin biopsies from patients with chronic dermatitis, as shown in FIG. 1E, although less than in psoriasis (FIG. 1C).

Figure 1F:
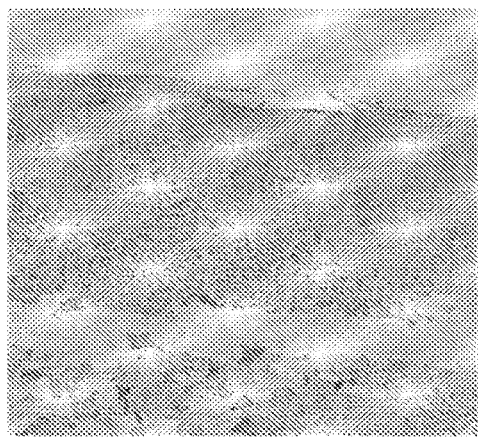

Moreover, a negative correlation between FABP4 and PPARγ expression was observed in keratinocytes and immune cells: while in normal skin PPARγ was detected throughout the epidermis and in few cells in the dermis, as shown in FIG. 1B, in psoriatic lesions the expression of PPARγ was significantly reduced and was displayed only in the uppermost layers of the epidermis, and not detected in dermal cells (FIG. 1D). PPARγ expression was also reduced in dermatitis skin biopsies, as shown in FIG. 1F. FABP5 was expressed only in keratinocytes from psoriatic skin, as previously reported ([16], not shown).

Figure 2A:
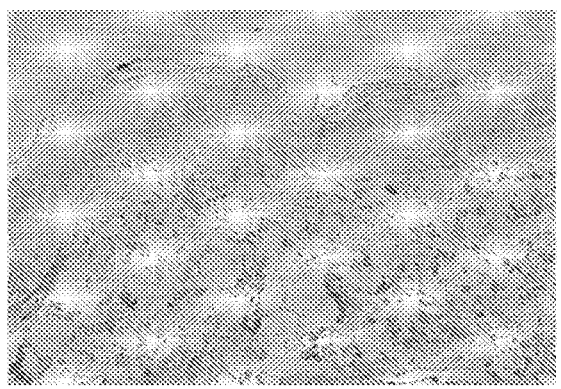
FIGS. 2A-2C show expression of FABP4 protein in immunohistochemistry staining of human skin: normal human skin (FIG. 2A), epidermis of psoriasis-involved skin (FIG. 2B), and dermis of psoriasis-involved skin (FIG. 2C). Tissue sections were stained with anti-FABP4 antibody. Original magnification ×200.
Figure 2B:
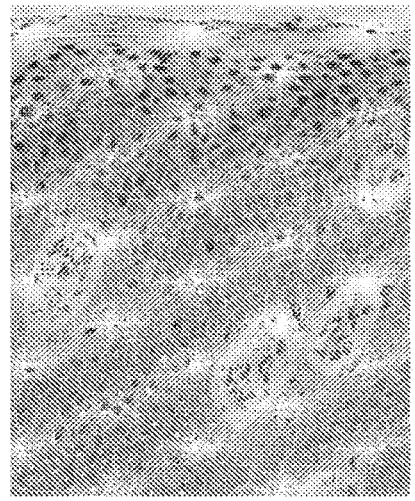
Figure 2C:
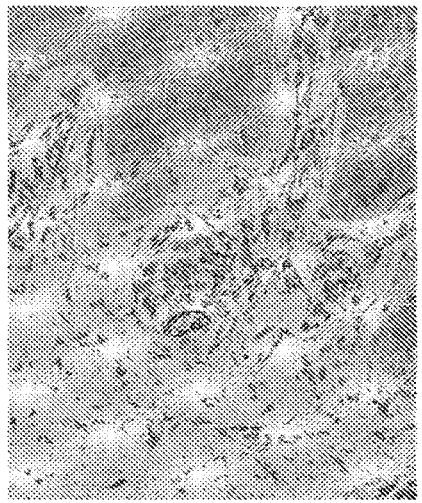
Figure 3A:
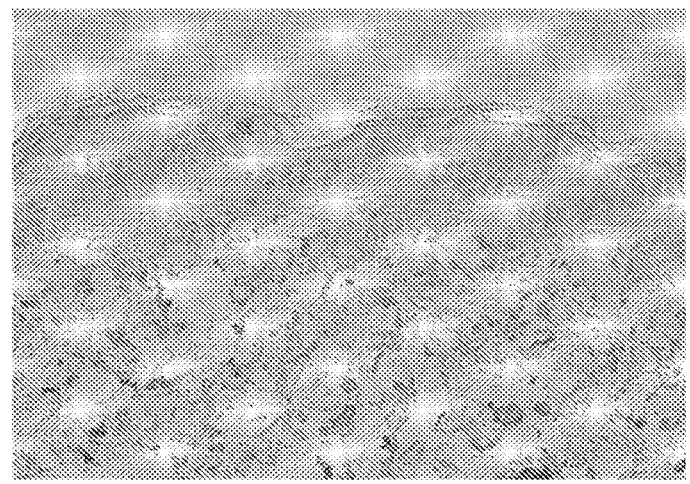
FIGS. 3A-3B show expression of PPARγ protein in immunohistochemistry staining of human skin: normal human skin (FIG. 3A), and psoriasis-involved skin (FIG. 3B). Tissue sections were stained with anti-PPARγ antibody. Original magnification ×200.
Figure 3B:
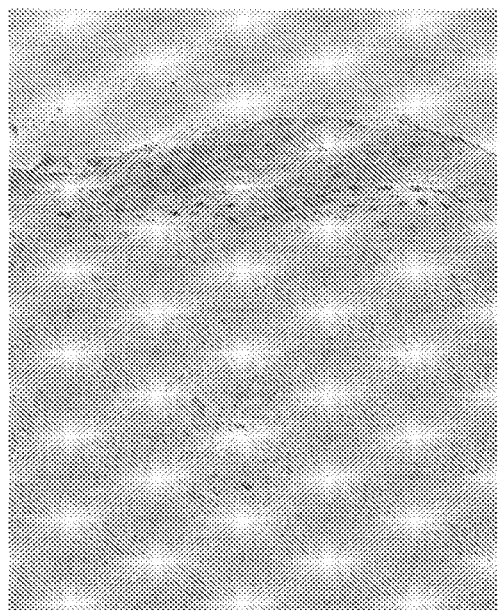

Psoriatic skin is characterized by a hyperproliferative epidermis comprised from multiple layers of keratinocytes, resulting in increased thickness of the skin. At higher magnification, FABP4 was demonstrated throughout the hyperplastic epidermis in psoriatic lesions, wherein staining was mostly cytoplasmic in the basal layers and nuclear in the upper layers, as shown in FIG. 2B. FABP4 expression in the dermis was predominantly observed in macrophages, lymphocytes and endothelial cells, in a cytoplasmic pattern, as shown in FIG. 2C. PPARγ expression in psoriatic skin was markedly reduced in the epidermis, appeared only in the uppermost layers, and was undetected in the dermis compared as to normal skin (see FIG. 3B versus 3A).

This suggests that the tendency to develop skin diseases having an inflammatory component may be detected by evaluating FABP, and particularly FABP4, expression in dermis and epidermis skin samples. It also suggests that FABP4 overexpression, and PPARγ downregulation, are linked to the pathogenesis of psoriasis.

Example 2: Tissue Expression Analysis of FABP4 in Human Cutaneous T Cell Lymphoma (CTCL) Skin Lesions CTCL is a group of neoplasms of skin-homing T cells. Mycosis fungoides (MF) represents the most common type of CTCL and accounts for approximately 50% of all primary cutaneous lymphomas. Although malignant in nature, MF has a protracted clinical course with inflammatory, dermatitis-like presentation [8].

The expression of FABP4 among patients with MF was studied by performing an immunohistochemical analysis of lesional skin. Samples from 5 patients with MF were tested and compared to normal human skin. Punch biopsies (6 mm in diameter) were obtained from patients with MF, from disease-involved skin. Normal skin was obtained from patients after surgical reduction of redundant skin. Tissue sections were processed and stained with anti-FABP4 antibody as described in Example 1.

Figure 4A:
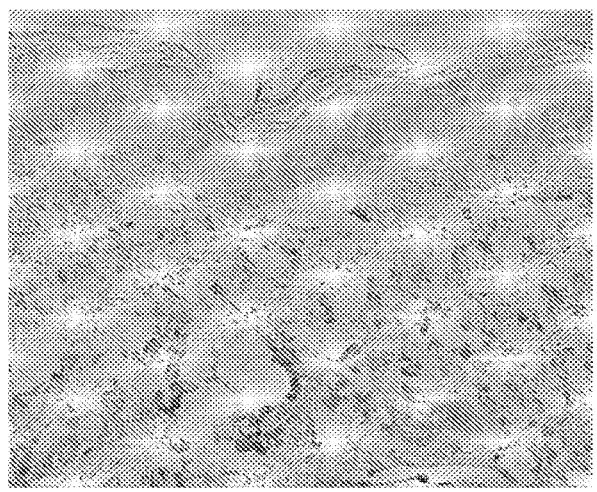
FIGS. 4A-4B are immunohistochemistry staining of FABP4 protein in human skin: normal skin (FIG. 4A), and human cutaneous T cell lymphoma (CTCL) skin lesions (FIG. 4B). Tissue sections were stained with anti-FABP4 antibody. Original magnification ×200.
Figure 4B:

High expression levels of FABP4 were observed in MF lesions compared to normal skin with all tested patients, as shown in FIGS. 4B and 4A, respectively. FABP4 expression was confined to the infiltrating T lymphocytes in the epidermis and the dermis. A strong cytoplasmic stain was observed in the dermal infiltrating cells, as well as in the malignant cells which penetrated the lower epidermis, which is the hallmark of MF.

Thus, due to the high expression of FABP4 protein in the malignant CTCL T-lymphocytes, detection of overexpression can be used to determine a patient's propensity towards development of CTCL or allow for early detection thereof.

Many dermatologic diseases (including psoriasis, dermatitis, and CTCL) are mediated by lymphocytes, predominantly T lymphocytes [17]. FABP4 expression has been reported in a restricted repertoire of cell types, only in macrophages, adipocytes and endothelial cells. In immunohistochemistry analysis performed by the present inventor, FABP4 was found to be expressed in inflammatory cells in the dermis, in both macrophages and lymphocytes. FABP4 expression in lymphocytes has not been reported so far, nor expression thereof in dermal cells in general, thus these findings are of high relevance in dermatological diseases.

Example 3: Overexpressing FABP4 in Primary Murine Keratinocytes

The introduction of FABP4 into keratinocytes was suggested to create a hyperproliferative state with impaired differentiation as seen in psoriasis. Differentiation was assessed by measuring the expression of two keratinocyte differentiation markers K1 and K5. K5 is a keratin whose level does not change during keratinocyte differentiation and therefore serves as a loading control, while K1 is induced during normal keratinocyte differentiation.

For assessing the effect of FABP4 overexpression in mouse primary keratinocytes, cells were infected with a lentiviral vector construct containing the FABP4 gene. The FABP4 lentiviral vector, named FABP4-T2A-EGFP, was constructed with the FABP4 gene under the CMV promotor, and contained the green fluorescence protein (GFP) gene as a reporter of expression. The presence of a T2A residue at the N-terminus of the FABP4 protein precludes FABP4 detection by anti-FABP4 commercial antibodies, due to interference with their binding. Therefore, anti-GFP antibodies for validation of infection and FABP4 overexpression were used instead.

For evaluating expression of K1 and K5 differentiation markers in primary murine keratinocytes with or without FABP4 expression, primary keratinocytes were prepared from neonatal mice as previously described [18], and infected with FABP4-T2A-EGFP vector. Two internal controls were used: cells which were not infected with the lentivirus and cells infected with the EGFP vector lacking the FABP4 gene. The cells were grown in differentiation media containing three different calcium concentrations. Elevation of extracellular calcium from low (0.05 mM) to medium (0.12 mM) or high (1 mM) concentration induced differentiation of keratinocytes.

Figure 5:
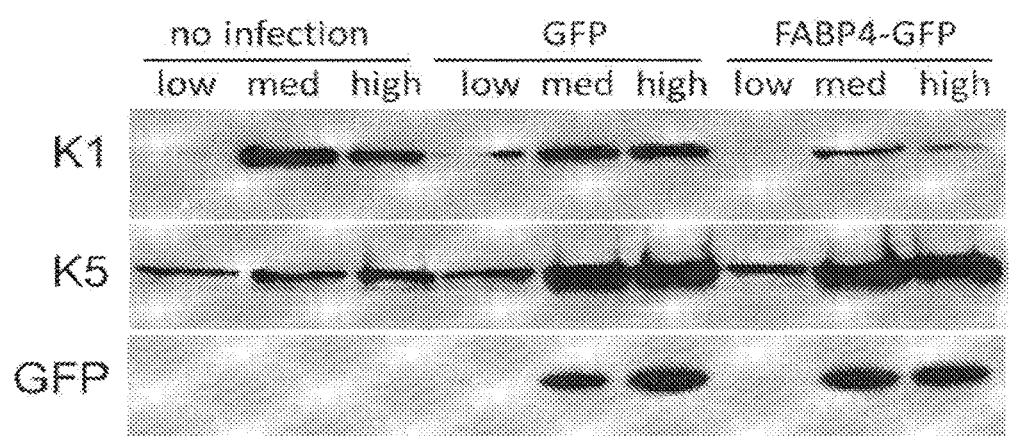
FIG. 5 is an immunoblot (Western Blotting) showing levels of keratinocyte differentiation markers K1 and K5 in primary murine keratinocytes overexpressing FABP4. The keratinocytes were infected with a lentiviral vector expressing FABP4 tagged with GFP (FABP4-GFP), lentiviral vector expressing GFP (GFP), or left untreated (no infection).

Expression of keratinocyte differentiation markers K1 and K5 in transfected and non-transfected cells is demonstrated in FIG. 5: infection with the lentivirus expressing FABP4-T2A-EGFP reduced the level of K1 both in medium and high calcium conditions compared to non-infected cells and GFP-infected cells. The level of K5 did not change during keratinocyte differentiation in absence of infection, as expected. The observation that FABP4 overexpression reduces K1 suggests that FABP4 interferes with the normal differentiation process of keratinocytes and promotes a hyperproliferative state, resembling psoriasis.

Example 4: Inhibition of FABP4 In Vivo in Imiquimod-Induced Psoriasis Model in Mice As already explained, psoriasis is a chronic inflammatory skin disorder. It occurs when the immune system mistakes the skin cells as a pathogen, and sends out faulty signals that speed up the proliferation of skin cells. Imiquimod (IMQ) is a potent immune activator that induces and exacerbates psoriasis when applied topically. Daily application of IMQ on mouse back skin induces inflamed scaly skin lesions resembling plaque type psoriasis [19, 20]. IMQ-induced psoriasis in mice has been long used as a model for human psoriasis.

The efficacy of oral administration of a FABP4-inhibitor to treat psoriasis in the IMQ-induced model in mice was tested.

BMS309403 (2-[[2'-(5-ethyl-3,4-diphenyl-1H-pyrazol-1-yl)[1,1'-biphenyl]-3-yl]oxy]-acetic acid, Formula I) was used as a FABP4-inhibitor:

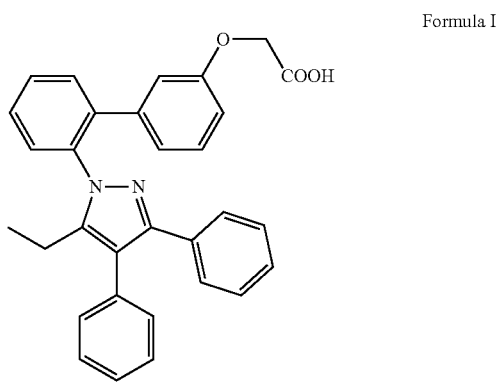 [SMILES: CCc1c(-c2ccccc2)c(-c2ccccc2)nn1-c1ccccc1-c1cccc(OCC(=O)O)c1]

Formula I

The test was carried out using Balb/c mice (Envigo RMS (Israel) Ltd), average (±SD) body weight at study initiation was 18.2±0.81g. Animals were fed ad libitum a commercial rodent diet (Teklad Certified Global 18% Protein Diet, Harlan cat #2018SC). Animals had free access to sterilized and acidified drinking water (pH between 2.5 and 3.5).

The tests included six groups of 3-10 mice per group, as follows:

one naïve (no IMQ) group;

one Vehicle control group, the vehicle formulation being 10% 1-methyl-2-pyrrolidone and 5% Cremophor EL in water for injection (WFI);

one treated group that received Cortisone acetate as a positive control—one tablet (25 mg each, Rekah Pharm) was triturated with a mortar. The powder was dissolved in 2.5 ml WFI yielding 10 mg/ml. The compound was administered per-os at 12.5 mg/kg BW (body weight) mouse of the compound once daily for six days starting the first day of IMQ application (Day 1); and three treated groups that received BMS (i.e. Test Item) at three doses—5, 15 and 30 mg/kg. BMS powder (Cayman Chemical) was dissolved in ethanol to create a 30 mg/ml solution. This stock solution was diluted in the Vehicle to create three different concentrations 0.5, 1.5 and 3 mg/ml. A new aqueous solution was prepared in each day. BMS was administered per-os once daily for six days starting the first day of IMQ application (Day 1).

IMQ-induction: A daily topical dose of 62.5 mg of commercially available IMQ cream (5%) (Aldara; 3M Pharmaceuticals) was applied to animals from all the groups except for the naïve group on the shaved back for six consecutive days, translated to a daily dose of 3.125 mg of the active compound.

Experiment conditions: All animals except for the naïve group received IMQ cream (Aldara TM 5% cream, #3 Pharmaceuticals) applied on the back skin daily for six consecutive days starting on Day 1 (-60 mg/mouse). The Test Item, Vehicle and Cortisone acetate were administered per-os daily for 6 days. During the study morbidity and mortality, body weight (BW), clinical signs, and Psoriasis Area and Severity Index (PASI) scoring were performed and representative pictures were taken. The animals were sacrificed on Day 9.

Scoring was performed by a trained observer in a "blinded" way, i.e., being unaware of the treatment. To score the severity of inflammation of the back skin, the clinical PASI scoring was employed. Erythema, scaling, and thickening were scored independently on a scale from 0 to 4: 0, none; 1, slight; 2, moderate; 3, marked; 4, very marked. The cumulative score (erythema plus scaling plus thickening), PASI scoring, served as a measure of the severity of inflammation (scale 0-12).

Mortality & morbidity: During both experiments, no animal died or was found in morbid conditions. No abnormal clinical signs were observed in any of the animals during the study. No effect of the treatment on body weight was detected.

Figure 6:
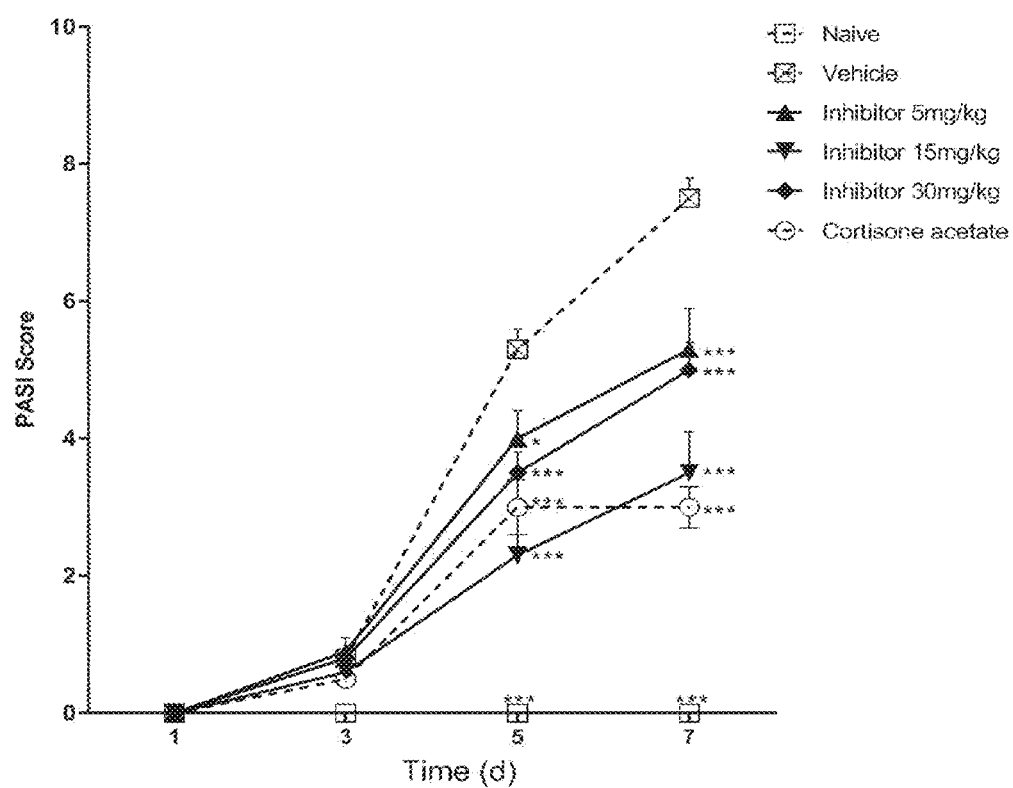
FIG. 6 shows Psoriasis Area Severity Index (PASI) scoring of the animals from the in vivo experiment at various time points. * $p<0.05$; *** $p<0.001$ compared to Vehicle group (using Two-way ANOVA followed by Bonferroni post-hoc test).
Figure 7:
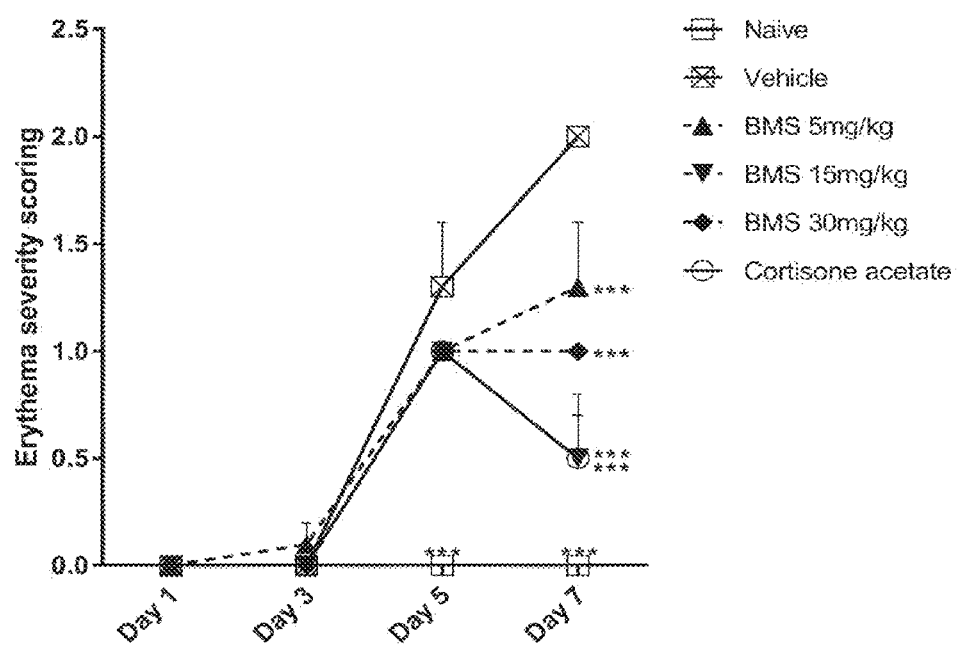
FIG. 7 shows erythema severity scoring of the animals from the in vivo experiment at various time points. *** $p<0.001$ compared to Vehicle group (using Two-way ANOVA followed by Bonferroni post-hoc test).
Figure 8:
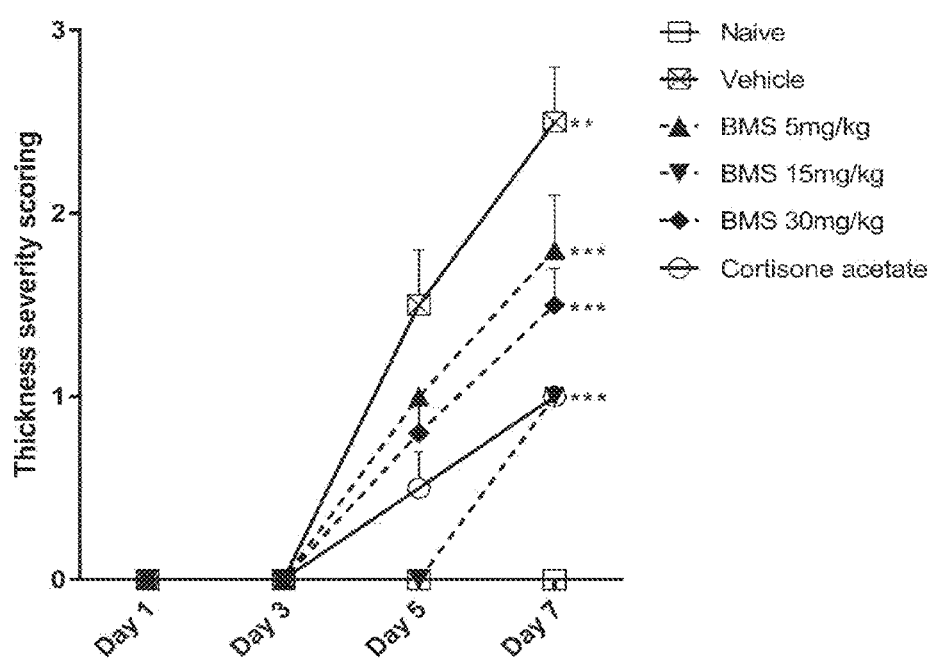
FIG. 8 shows skin thickness severity scoring of the animals from the in vivo experiment at various time points.  $p<0.01$; * $p<0.001$ compared to Vehicle group (using Two-way ANOVA followed by Bonferroni post-hoc test).
Figure 9:
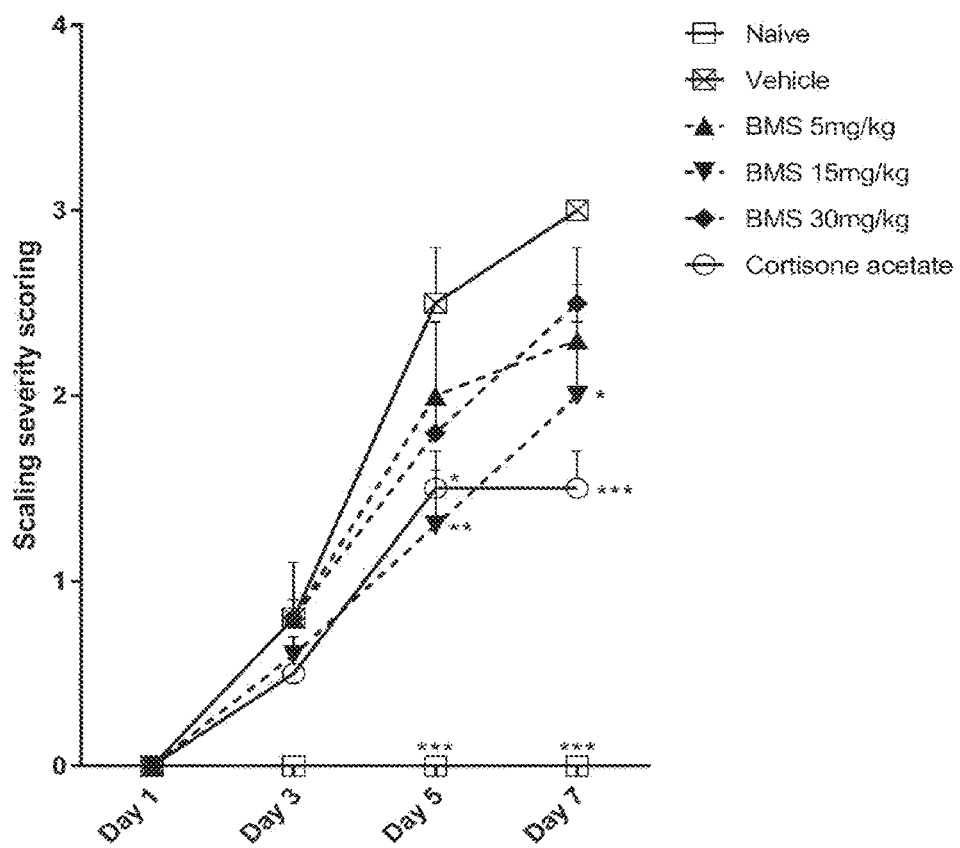
FIG. 9 shows scaling severity scoring of the animals from the in vivo experiment at various time points. *$p<0.05$,  $p<0.01$; * $p<0.001$ compared to Vehicle group (using Two-way ANOVA followed by Bonferroni post-hoc test).
Figure 10A:
FIGS. 10A-10F are representative pictures of mice on Day 7 of the in vivo experiment: Naïve (FIG. 10A), Vehicle (FIG. 10B), BMS 5 mg/kg (FIG. 10C), BMS 15 mg/kg (FIG. 10D), BMS 30 mg/kg (FIG. 10E), and Cortisone acetate (FIG. 10F).
Figure 10B:
Figure 10C:
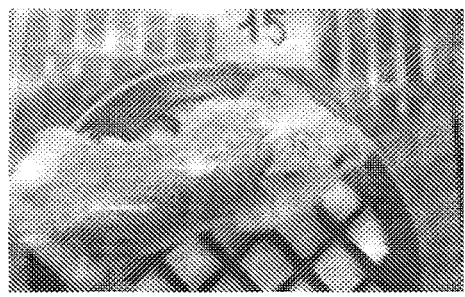
Figure 10D:
Figure 10E:
Figure 10F:

Scoring severity of skin inflammation: The average score of the severity of inflammation of the back skin, i.e. the PASI, is presented in FIG. 6. Each parameter, namely erythema severity, skin thickness, and scaling, was measured individually (FIGS. 7-9, respectively). According to the PASI scoring, all IMQ treated groups developed considerable skin reaction, as compared to the naïve group, notably on Days 5 and 7 of the study. On Day 7 significant amelioration of the skin inflammation by the BMS treatment was observed. The middle dose of BMS (15 mg/kg) seemed to have the highest impact on the inflammation severity. This dose exhibited the best results on the tested parameters—erythema, skin thickness and scaling. Representative pictures taken at Day 7 are shown in FIGS. 10A-10F.

In summary, all IMQ treated groups developed considerable skin reaction, as compared to the naïve group, notably on Days 5 and 7 of the study. On Day 7 significant amelioration of the effect was observed in the BMS treated groups for all test parameters, i.e. inflammation severity, erythema, skin thickness and scaling. The experiment was repeated tree times with similar results.

---

The invention claimed is:

1. A method for treating or preventing a skin disease in a subject in need thereof having, in the skin thereof, keratinocytes or inflammatory cells that overexpress FABP4, said method comprising administering to said subject a therapeutically effective amount of at least one small molecule FABP4 inhibitor or a pharmaceutical composition thereof, wherein said at least one small molecule FABP4 inhibitor each independently has a main ring structure which has a 3-10 membered saturated, unsaturated, or aromatic carbocyclic or heterocyclic ring, or a system of two or more such rings that are fused, bridged, or spiro-connected, and wherein said main ring structure is optionally substituted at one or more of its possible substitution positions; and wherein said skin disease is characterized by the presence, in the skin, of keratinocytes or inflammatory cells overexpressing FAPB4.

2. The method of claim 1, further comprising administering a PPARγ agonist to the subject.

3. The method of claim 2, wherein said PPARγ agonist is administered concomitantly with said at least one small molecule FABP4 inhibitor.

4. The method of claim 2, wherein said small molecule FABP4 inhibitor and said PPARγ agonist are administered sequentially.

5. The method of claim 1, wherein said at least one small molecule FABP4-inhibitor has a molecular weight of up to about 1000 Da.

6. The method of claim 1, wherein said at least one small molecule FABP4 inhibitor is selected from the group consisting of a carbazole alkanoic acid, an aryl sulfonamide, a sulfonylthiophene, a hydroxypyrimidine, a carbazole, a tetrahydrocarbazole, an indole, a 2,3-dimethylindole, a benzoylbenzene, a biphenyl-alkanoic acid, an oxazole-alkanoic acid, a pyrimidine, a tetrahydropyrimidine, a pyrimidone, a derivative, a pyridine, a pyrazine, a pyrazinone, a tetrazole, a triazolopyrimidine, a triazolopyrimidinone, a pyrazole, a quinolone, an aryl carboxylic acid, and a flavonoid.

7. The method of claim 6, wherein said small molecule FABP4 inhibitor is a carbazole alkanoic acid and said carbazole alkanoic acid is carbazole butanoic acid; said small molecule FABP4 inhibitor is a hydroxypyrimidine and said hydroxypyrimidine is 4-hydroxypyrimidine or 2-hydroxypyrimidine; said small molecule FABP4 inhibitor is an oxazole-alkanoic acid and said oxazole-alkanoic acid is 2-oxazole-alkanoic acid; or said small molecule FABP4 inhibitor is a flavonoid and said flavonoid is a flavanol, flavanone or isoflavone.

8. The method of claim 1, wherein said small molecule FABP4 inhibitor is both an FABP4 inhibitor and an FABP5 inhibitor.

9. The method of claim 2, wherein said PPARγ agonist is selected from the group consisting of thiazolidinedione, pioglitazone, rosiglitazone, lobeglitazone, ciglitazone, darglitazone, englitazone, netoglitazone, rivoglitazone, troglitazone, rhodamine, and a non-steroidal anti-inflammatory drug.

10. The method of claim 1, wherein said skin disease is selected from the group consisting of psoriasis, dermatitis (atopic, seborrheic, contact), eczema, parapsoriasis, lichen planus, lichen plano-pilaris, *pityriasis* lichenoides et varioliformis *acuta, pityriasis* lichenoides chronica, *pityriasis rubra* pilaris, *pityriasis rosea*, graft-versus-host disease, histiocytoses, drug-induced eruptions, autoimmune connective tissue diseases, rosacea, folliculitis, acne, warts, ichthyosis, vitiligo, scarring alopecia, cutaneous T cell lymphoma (CTCL), actinic keratosis, squamous cell carcinoma, basal cell carcinoma, nevus, lichen simplex chronicus, xerosis, keratosis, keratoderma, pruritus, a burn, a scar, a callus, and a keloid.

11. The method of claim 1, wherein the skin disease is psoriasis.

12. The method of claim 10, wherein the skin disease is CTCL.

13. The method of claim 10, wherein said skin disease is lichen planus/lichen planopilaris.

14. The method of claim 10, wherein said skin disease is dermatitis.

15. The method of claim 1, wherein the skin disease is an inflammatory skin disease.

16. The method of claim 1, wherein said at least one small molecule FABP4 inhibitor is administered topically, orally, by inhalation, nasally, transdermally, ocularly, or parenterally into the circulatory system of said subject.

17. The method of claim 6, wherein said small molecule FABP4 inhibitor is a carbazole alkanoic acid, and said carbazole alkanoic acid is carbazole butanoic acid.

18. The method of claim 1, wherein said main ring structure is substituted with one or more groups each independently selected from the group consisting of alkoxy, alkylthio, halide, pseudohalide, haloalkyl, haloalkoxy, ester, ether, alkanoic acid, amino, sulphinyl, sulphonyl, sulpho, mono- or dialkylaminocarbonyl, carboxamide, amido, thioamido, oxyamido, thiaamido, dithiamido, ureido, thioureido, and formamido.

* * * * *